US010604566B2

(12) United States Patent
Vandeghinste et al.

(10) Patent No.: US 10,604,566 B2
(45) Date of Patent: Mar. 31, 2020

(54) ANTAGONISTS OF IL-17C FOR THE TREATMENT AND/OR PREVENTION OF ATOPIC DERMATITIS

(71) Applicants: MORPHOSYS AG, Planegg (DE); GALAPAGOS NV, Mechelen (BE)

(72) Inventors: Nick Ernest René Vandeghinste, Mechelen (BE); Reginald Christophe Xavier Brys, Mechelen (BE)

(73) Assignees: Galapagos NV, Mechelen (BE); MorphoSys AG, Martinsfried/Planegg (DE)

( * ) Notice: Subject to any disclaimer, the term of this patent is extended or adjusted under 35 U.S.C. 154(b) by 0 days.

(21) Appl. No.: 15/764,918

(22) PCT Filed: Oct. 5, 2016

(86) PCT No.: PCT/EP2016/073776
§ 371 (c)(1),
(2) Date: Mar. 30, 2018

(87) PCT Pub. No.: WO2017/060289
PCT Pub. Date: Apr. 13, 2017

(65) Prior Publication Data
US 2018/0273614 A1  Sep. 27, 2018

(30) Foreign Application Priority Data

Oct. 5, 2015  (EP) .................................... 15188355

(51) Int. Cl.
*C07K 16/24*     (2006.01)
*A61K 39/395*    (2006.01)
*A61K 31/573*    (2006.01)
*A61K 45/06*     (2006.01)
*C07K 14/54*     (2006.01)
*A61K 39/00*     (2006.01)

(52) U.S. Cl.
CPC .......... *C07K 16/244* (2013.01); *A61K 31/573* (2013.01); *A61K 39/3955* (2013.01); *A61K 45/06* (2013.01); *A61K 2039/505* (2013.01); *A61K 2039/545* (2013.01); *C07K 2317/21* (2013.01); *C07K 2317/24* (2013.01); *C07K 2317/565* (2013.01); *C07K 2317/76* (2013.01)

(58) Field of Classification Search
CPC .............. C07K 16/244; C07K 2317/76; C07K 2317/92; C07K 14/7155; A61K 2039/505; A61K 2300/00; A61K 38/00; A61K 39/3955; C12N 15/625; G01N 33/686; G01N 33/6893
See application file for complete search history.

(56) References Cited

U.S. PATENT DOCUMENTS

2007/0049525 A1* 3/2007 Gao ..................... A61K 39/395
                                                424/133.1
2008/0044432 A1* 2/2008 Gorman ............... C07K 14/715
                                                424/184.1

FOREIGN PATENT DOCUMENTS

| WO | 99/60127      | 11/1999 |
| WO | 2006/044840   | 4/2006  |
| WO | 2007/047738   | 4/2007  |
| WO | 2008/049070   | 4/2008  |
| WO | 2013/016220   | 1/2013  |
| WO | 2013/057241   | 4/2013  |
| WO | 2013/186236   | 12/2013 |

OTHER PUBLICATIONS

Brummell et al. (Biochemistry 32:1180-1187 (1993)).*
Kobayashi et al. (Protein Engineering 12:879-844 (1999)).*
Brorson et al. (J. Immunol. 163:6694-6701 (1999)).*
Colman (Research in Immunol. 145:33-36 (1994)).*
Langa et al, South African family practice, 2011; vol. 53, No. 4, pp. 340-346.*
Reich et al, Expert Rev. Dermatology; 2013; vol. 8;, No. 3, pp. 291-299.*
Extended European Search Report in EP 15188355.0 dated Mar. 16, 2016.
Brunner et al. "CCL7 contributes to the TNF-alpha-dependent inflammation of lesion psoriatic skin" Experimental Dermatology 2015 24:522-528.
Chang et al. "Interleukin-17C promotes Th17 cell responses and autoimmune disease via interleukin-17 receptor E" Immunity 2011 35:611-621.
Li et al. "Cloning and characterization of IL-17B and IL-17C, two new members of the IL-17 cytokine family" Proc Natl Acad Sci USA 2000 97:773-778.
Ramirez-Carrozzi et al. "IL-17C regulates the innate immune function of epithelial cells in an autocrine manner" Nature Immunology 2011 12:1159-1166.
Song et al. "Alterations in the microbiota drive interleukin-17C production from intestinal epithelial cells to promote tumorigenesis" Immunity 2014 40:140-152.
Song et al. "IL-17RE is the functional receptor for IL-17C and mediates mucosal immunity to infection with intestinal pathogens" Nature Immunology 2011 12:1151-1158.
Yamaguchi et al. "IL-17B and IL-17C are associated with TNF-alpha production and contribute to the exacerbation of inflammatory arthritis" J. Immunol 2007 179:7128-3716.
International Search Report and Written Opinion in PCT/EP2016/073776 dated Dec. 19, 2016.
International Preliminary Report on Patentability in PCT/EP2016/073776 dated Apr. 10, 2018.

* cited by examiner

*Primary Examiner* — Bridget E Bunner
*Assistant Examiner* — Fozia Hamud
(74) *Attorney, Agent, or Firm* — Leslie Fischer

(57) ABSTRACT

The present invention provides antagonists of IL-17C for use in the treatment and/or prevention of atopic dermatitis and related conditions.

6 Claims, 9 Drawing Sheets
Specification includes a Sequence Listing.

SEQUENCE LISTING

<160> NUMBER OF SEQ ID NOS: 23

<210> SEQ ID NO 1
<211> LENGTH: 197
<212> TYPE: PRT
<213> ORGANISM: Homo sapiens

<400> SEQUENCE: 1

```
Met Thr Leu Leu Pro Gly Leu Leu Phe Leu Thr Trp Leu His Thr Cys
1               5                   10                  15

Leu Ala His His Asp Pro Ser Leu Arg Gly His Pro His Ser His Gly
            20                  25                  30

Thr Pro His Cys Tyr Ser Ala Glu Glu Leu Pro Leu Gly Gln Ala Pro
        35                  40                  45

Pro His Leu Leu Ala Arg Gly Ala Lys Trp Gly Gln Ala Leu Pro Val
    50                  55                  60

Ala Leu Val Ser Ser Leu Glu Ala Ala Ser His Arg Gly Arg His Glu
65                  70                  75                  80

Arg Pro Ser Ala Thr Thr Gln Cys Pro Val Leu Arg Pro Glu Glu Val
                85                  90                  95

Leu Glu Ala Asp Thr His Gln Arg Ser Ile Ser Pro Trp Arg Tyr Arg
            100                 105                 110

Val Asp Thr Asp Glu Asp Arg Tyr Pro Gln Lys Leu Ala Phe Ala Glu
        115                 120                 125

Cys Leu Cys Arg Gly Cys Ile Asp Ala Arg Thr Gly Arg Glu Thr Ala
    130                 135                 140

Ala Leu Asn Ser Val Arg Leu Leu Gln Ser Leu Leu Val Leu Arg Arg
145                 150                 155                 160

Arg Pro Cys Ser Arg Asp Gly Ser Gly Leu Pro Thr Pro Gly Ala Phe
```

```
                        165                 170                 175
Ala Phe His Thr Glu Phe Ile His Val Pro Val Gly Cys Thr Cys Val
                180                 185                 190

Leu Pro Arg Ser Val
        195

<210> SEQ ID NO 2
<211> LENGTH: 866
<212> TYPE: PRT
<213> ORGANISM: Homo sapiens

<400> SEQUENCE: 2

Met Gly Ala Ala Arg Ser Pro Pro Ser Ala Val Pro Gly Pro Leu Leu
1               5                   10                  15

Gly Leu Leu Leu Leu Leu Leu Gly Val Leu Ala Pro Gly Gly Ala Ser
            20                  25                  30

Leu Arg Leu Leu Asp His Arg Ala Leu Val Cys Ser Gln Pro Gly Leu
        35                  40                  45

Asn Cys Thr Val Lys Asn Ser Thr Cys Leu Asp Asp Ser Trp Ile His
    50                  55                  60

Pro Arg Asn Leu Thr Pro Ser Pro Lys Asp Leu Gln Ile Gln Leu
65                  70                  75                  80

His Phe Ala His Thr Gln Gln Gly Asp Leu Phe Pro Val Ala His Ile
                85                  90                  95

Glu Trp Thr Leu Gln Thr Asp Ala Ser Ile Leu Tyr Leu Glu Gly Ala
            100                 105                 110

Glu Leu Ser Val Leu Gln Leu Asn Thr Asn Glu Arg Leu Cys Val Arg
        115                 120                 125

Phe Glu Phe Leu Ser Lys Leu Arg His His Arg Arg Trp Arg Phe
    130                 135                 140

Thr Phe Ser His Phe Val Val Asp Pro Asp Gln Glu Tyr Glu Val Thr
145                 150                 155                 160

Val His His Leu Pro Lys Pro Ile Pro Asp Gly Asp Pro Asn His Gln
                165                 170                 175

Ser Lys Asn Phe Leu Val Pro Asp Cys Glu His Ala Arg Met Lys Val
            180                 185                 190

Thr Thr Pro Cys Met Ser Ser Gly Ser Leu Trp Asp Pro Asn Ile Thr
        195                 200                 205

Val Glu Thr Leu Glu Ala His Gln Leu Arg Val Ser Phe Thr Leu Trp
    210                 215                 220

Asn Glu Ser Thr His Tyr Gln Ile Leu Leu Thr Ser Phe Pro His Met
225                 230                 235                 240

Glu Asn His Ser Cys Phe Glu His Met His His Ile Pro Ala Pro Arg
                245                 250                 255

Pro Glu Glu Phe His Gln Arg Ser Asn Val Thr Leu Thr Leu Arg Asn
            260                 265                 270

Leu Lys Gly Cys Cys Arg His Gln Val Gln Ile Gln Pro Phe Phe Ser
        275                 280                 285

Ser Cys Leu Asn Asp Cys Leu Arg His Ser Ala Thr Val Ser Cys Pro
    290                 295                 300

Glu Met Pro Asp Thr Pro Glu Pro Ile Pro Asp Tyr Met Pro Leu Trp
305                 310                 315                 320

Val Tyr Trp Phe Ile Thr Gly Ile Ser Ile Leu Leu Val Gly Ser Val
                325                 330                 335
```

```
Ile Leu Leu Ile Val Cys Met Thr Trp Arg Leu Ala Gly Pro Gly Ser
                340                 345                 350

Glu Lys Tyr Ser Asp Asp Thr Lys Tyr Thr Asp Gly Leu Pro Ala Ala
        355                 360                 365

Asp Leu Ile Pro Pro Leu Lys Pro Arg Lys Val Trp Ile Ile Tyr
    370                 375                 380

Ser Ala Asp His Pro Leu Tyr Val Asp Val Val Leu Lys Phe Ala Gln
385                 390                 395                 400

Phe Leu Leu Thr Ala Cys Gly Thr Glu Val Ala Leu Asp Leu Leu Glu
                405                 410                 415

Glu Gln Ala Ile Ser Glu Ala Gly Val Met Thr Trp Val Gly Arg Gln
                420                 425                 430

Lys Gln Glu Met Val Glu Ser Asn Ser Lys Ile Ile Val Leu Cys Ser
                435                 440                 445

Arg Gly Thr Arg Ala Lys Trp Gln Ala Leu Leu Gly Arg Gly Ala Pro
            450                 455                 460

Val Arg Leu Arg Cys Asp His Gly Lys Pro Val Gly Asp Leu Phe Thr
465                 470                 475                 480

Ala Ala Met Asn Met Ile Leu Pro Asp Phe Lys Arg Pro Ala Cys Phe
                485                 490                 495

Gly Thr Tyr Val Val Cys Tyr Phe Ser Glu Val Ser Cys Asp Gly Asp
            500                 505                 510

Val Pro Asp Leu Phe Gly Ala Ala Pro Arg Tyr Pro Leu Met Asp Arg
            515                 520                 525

Phe Glu Glu Val Tyr Phe Arg Ile Gln Asp Leu Glu Met Phe Gln Pro
    530                 535                 540

Gly Arg Met His Arg Val Gly Glu Leu Ser Gly Asp Asn Tyr Leu Arg
545                 550                 555                 560

Ser Pro Gly Gly Arg Gln Leu Arg Ala Ala Leu Asp Arg Phe Arg Asp
                565                 570                 575

Trp Gln Val Arg Cys Pro Asp Trp Phe Glu Cys Glu Asn Leu Tyr Ser
                580                 585                 590

Ala Asp Asp Gln Asp Ala Pro Ser Leu Asp Glu Glu Val Phe Glu Glu
                595                 600                 605

Pro Leu Leu Pro Pro Gly Thr Gly Ile Val Lys Arg Ala Pro Leu Val
    610                 615                 620

Arg Glu Pro Gly Ser Gln Ala Cys Leu Ala Ile Asp Pro Leu Val Gly
625                 630                 635                 640

Glu Glu Gly Gly Ala Ala Val Ala Lys Leu Glu Pro His Leu Gln Pro
                645                 650                 655

Arg Gly Gln Pro Ala Pro Gln Pro Leu His Thr Leu Val Leu Ala Ala
                660                 665                 670

Glu Glu Gly Ala Leu Val Ala Ala Val Glu Pro Gly Pro Leu Ala Asp
            675                 680                 685

Gly Ala Ala Val Arg Leu Ala Leu Ala Gly Glu Gly Glu Ala Cys Pro
            690                 695                 700

Leu Leu Gly Ser Pro Gly Ala Gly Arg Asn Ser Val Leu Phe Leu Pro
705                 710                 715                 720

Val Asp Pro Glu Asp Ser Pro Leu Gly Ser Ser Thr Pro Met Ala Ser
                725                 730                 735

Pro Asp Leu Leu Pro Glu Asp Val Arg Glu His Leu Glu Gly Leu Met
            740                 745                 750

Leu Ser Leu Phe Glu Gln Ser Leu Ser Cys Gln Ala Gln Gly Gly Cys
```

```
                755                 760                 765
Ser Arg Pro Ala Met Val Leu Thr Asp Pro His Thr Pro Tyr Glu Glu
770                 775                 780

Glu Gln Arg Gln Ser Val Gln Ser Asp Gln Gly Tyr Ile Ser Arg Ser
785                 790                 795                 800

Ser Pro Gln Pro Pro Glu Gly Leu Thr Glu Met Glu Glu Glu Glu Glu
                805                 810                 815

Glu Glu Gln Asp Pro Gly Lys Pro Ala Leu Pro Leu Ser Pro Glu Asp
                820                 825                 830

Leu Glu Ser Leu Arg Ser Leu Gln Arg Gln Leu Leu Phe Arg Gln Leu
                835                 840                 845

Gln Lys Asn Ser Gly Trp Asp Thr Met Gly Ser Glu Ser Glu Gly Pro
850                 855                 860

Ser Ala
865

<210> SEQ ID NO 3
<211> LENGTH: 667
<212> TYPE: PRT
<213> ORGANISM: Homo sapiens

<400> SEQUENCE: 3

Met Gly Ser Ser Arg Leu Ala Ala Leu Leu Pro Leu Leu Leu Leu Ile
1               5                   10                  15

Val Ile Asp Leu Ser Asp Ser Ala Gly Ile Gly Phe Arg His Leu Pro
                20                  25                  30

His Trp Asn Thr Arg Cys Pro Leu Ala Ser His Thr Asp Asp Ser Phe
            35                  40                  45

Thr Gly Ser Ser Ala Tyr Ile Pro Cys Arg Thr Trp Trp Ala Leu Phe
        50                  55                  60

Ser Thr Lys Pro Trp Cys Val Arg Val Trp His Cys Ser Arg Cys Leu
65                  70                  75                  80

Cys Gln His Leu Leu Ser Gly Gly Ser Gly Leu Gln Arg Gly Leu Phe
                85                  90                  95

His Leu Leu Val Gln Lys Ser Lys Lys Ser Ser Thr Phe Lys Phe Tyr
            100                 105                 110

Arg Arg His Lys Met Pro Ala Pro Ala Gln Arg Lys Leu Leu Pro Arg
        115                 120                 125

Arg His Leu Ser Glu Lys Ser His His Ile Ser Ile Pro Ser Pro Asp
130                 135                 140

Ile Ser His Lys Gly Leu Arg Ser Lys Arg Thr Gln Pro Ser Asp Pro
145                 150                 155                 160

Glu Thr Trp Glu Ser Leu Pro Arg Leu Asp Ser Gln Arg His Gly Gly
                165                 170                 175

Pro Glu Phe Ser Phe Asp Leu Leu Pro Glu Ala Arg Ala Ile Arg Val
            180                 185                 190

Thr Ile Ser Ser Gly Pro Glu Val Ser Val Arg Leu Cys His Gln Trp
        195                 200                 205

Ala Leu Glu Cys Glu Glu Leu Ser Ser Pro Tyr Asp Val Gln Lys Ile
    210                 215                 220

Val Ser Gly Gly His Thr Val Glu Leu Pro Tyr Glu Phe Leu Leu Pro
225                 230                 235                 240

Cys Leu Cys Ile Glu Ala Ser Tyr Leu Gln Glu Asp Thr Val Arg Arg
                245                 250                 255
```

-continued

```
Lys Lys Cys Pro Phe Gln Ser Trp Pro Glu Ala Tyr Gly Ser Asp Phe
            260                 265                 270

Trp Lys Ser Val His Phe Thr Asp Tyr Ser Gln His Thr Gln Met Val
        275                 280                 285

Met Ala Leu Thr Leu Arg Cys Pro Leu Lys Leu Glu Ala Ala Leu Cys
    290                 295                 300

Gln Arg His Asp Trp His Thr Leu Cys Lys Asp Leu Pro Asn Ala Thr
305                 310                 315                 320

Ala Arg Glu Ser Asp Gly Trp Tyr Val Leu Lys Val Asp Leu His
                325                 330                 335

Pro Gln Leu Cys Phe Lys Phe Ser Phe Gly Asn Ser Ser His Val Glu
            340                 345                 350

Cys Pro His Gln Thr Gly Ser Leu Thr Ser Trp Asn Val Ser Met Asp
        355                 360                 365

Thr Gln Ala Gln Gln Leu Ile Leu His Phe Ser Ser Arg Met His Ala
    370                 375                 380

Thr Phe Ser Ala Ala Trp Ser Leu Pro Gly Leu Gly Gln Asp Thr Leu
385                 390                 395                 400

Val Pro Pro Val Tyr Thr Val Ser Gln Ala Arg Gly Ser Ser Pro Val
                405                 410                 415

Ser Leu Asp Leu Ile Ile Pro Phe Leu Arg Pro Gly Cys Cys Val Leu
            420                 425                 430

Val Trp Arg Ser Asp Val Gln Phe Ala Trp Lys His Leu Leu Cys Pro
        435                 440                 445

Asp Val Ser Tyr Arg His Leu Gly Leu Leu Ile Leu Ala Leu Leu Ala
    450                 455                 460

Leu Leu Thr Leu Leu Gly Val Val Leu Ala Leu Thr Cys Arg Arg Pro
465                 470                 475                 480

Gln Ser Gly Pro Gly Pro Ala Arg Pro Val Leu Leu Leu His Ala Ala
                485                 490                 495

Asp Ser Glu Ala Gln Arg Arg Leu Val Gly Ala Leu Ala Glu Leu Leu
            500                 505                 510

Arg Ala Ala Leu Gly Gly Gly Arg Asp Val Ile Val Asp Leu Trp Glu
        515                 520                 525

Gly Arg His Val Ala Arg Val Gly Pro Leu Pro Trp Leu Trp Ala Ala
    530                 535                 540

Arg Thr Arg Val Ala Arg Glu Gln Gly Thr Val Leu Leu Leu Trp Ser
545                 550                 555                 560

Gly Ala Asp Leu Arg Pro Val Ser Gly Pro Asp Pro Arg Ala Ala Pro
                565                 570                 575

Leu Leu Ala Leu Leu His Ala Ala Pro Arg Pro Leu Leu Leu Leu Ala
            580                 585                 590

Tyr Phe Ser Arg Leu Cys Ala Lys Gly Asp Ile Pro Pro Pro Leu Arg
        595                 600                 605

Ala Leu Pro Arg Tyr Arg Leu Leu Arg Asp Leu Pro Arg Leu Leu Arg
    610                 615                 620

Ala Leu Asp Ala Arg Pro Phe Ala Glu Ala Thr Ser Trp Gly Arg Leu
625                 630                 635                 640

Gly Ala Arg Gln Arg Arg Gln Ser Arg Leu Glu Leu Cys Ser Arg Leu
                645                 650                 655

Glu Arg Glu Ala Ala Arg Leu Ala Asp Leu Gly
            660                 665
```

```
<210> SEQ ID NO 4
<211> LENGTH: 10
<212> TYPE: PRT
<213> ORGANISM: Artificial Sequence
<220> FEATURE:
<223> OTHER INFORMATION: mab library

<400> SEQUENCE: 4

Gly Tyr Thr Phe Thr Ser Asn Phe Ile His
1               5                   10

<210> SEQ ID NO 5
<211> LENGTH: 20
<212> TYPE: PRT
<213> ORGANISM: Artificial Sequence
<220> FEATURE:
<223> OTHER INFORMATION: mab library

<400> SEQUENCE: 5

Trp Met Gly Trp Ile Ser Pro Tyr Asn Gly Asp Thr Asn Tyr Ala Gln
1               5                   10                  15

Lys Phe Gln Gly
            20

<210> SEQ ID NO 6
<211> LENGTH: 16
<212> TYPE: PRT
<213> ORGANISM: Artificial Sequence
<220> FEATURE:
<223> OTHER INFORMATION: mab Library

<400> SEQUENCE: 6

Glu Ser Val Tyr Tyr Gly Ser Asp Tyr Gly Tyr Asn Gly Met Asp Ile
1               5                   10                  15

<210> SEQ ID NO 7
<211> LENGTH: 11
<212> TYPE: PRT
<213> ORGANISM: Artificial Sequence
<220> FEATURE:
<223> OTHER INFORMATION: mab Library

<400> SEQUENCE: 7

Ser Gly Asp Asn Leu Gly Glu Glu Tyr Val Ser
1               5                   10

<210> SEQ ID NO 8
<211> LENGTH: 11
<212> TYPE: PRT
<213> ORGANISM: Artificial Sequence
<220> FEATURE:
<223> OTHER INFORMATION: mab Library

<400> SEQUENCE: 8

Leu Val Ile Tyr Asp Asp Thr Lys Arg Pro Ser
1               5                   10

<210> SEQ ID NO 9
<211> LENGTH: 9
<212> TYPE: PRT
<213> ORGANISM: Artificial Sequence
<220> FEATURE:
<223> OTHER INFORMATION: mab Library

<400> SEQUENCE: 9

Ala Ser Trp Asp Leu Trp Ser Val Glu
1               5
```

<210> SEQ ID NO 10
<211> LENGTH: 109
<212> TYPE: PRT
<213> ORGANISM: Artificial Sequence
<220> FEATURE:
<223> OTHER INFORMATION: mab Library

<400> SEQUENCE: 10

```
Asp Ile Glu Leu Thr Gln Pro Pro Ser Val Ser Val Ser Pro Gly Gln
1               5                   10                  15

Thr Ala Ser Ile Thr Cys Ser Gly Asp Asn Leu Gly Glu Glu Tyr Val
            20                  25                  30

Ser Trp Tyr Gln Gln Lys Pro Gly Gln Ala Pro Val Leu Val Ile Tyr
        35                  40                  45

Asp Asp Thr Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Ala Ser Trp Asp Leu Trp Ser Val Glu
                85                  90                  95

Val Phe Gly Gly Gly Thr Lys Leu Thr Val Leu Gly Gln
            100                 105
```

<210> SEQ ID NO 11
<211> LENGTH: 125
<212> TYPE: PRT
<213> ORGANISM: Artificial Sequence
<220> FEATURE:
<223> OTHER INFORMATION: mab Library

<400> SEQUENCE: 11

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Asn
            20                  25                  30

Phe Ile His Trp Val Arg Gln Ala Pro Gly Gln Gly Leu Glu Trp Met
        35                  40                  45

Gly Trp Ile Ser Pro Tyr Asn Gly Asp Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Glu Asp Thr Ala Val Tyr Tyr Cys
                85                  90                  95

Ala Arg Glu Ser Val Tyr Tyr Gly Ser Asp Tyr Gly Tyr Asn Gly Met
            100                 105                 110

Asp Ile Trp Gly Gln Gly Thr Leu Val Thr Val Ser Ser
        115                 120                 125
```

<210> SEQ ID NO 12
<211> LENGTH: 327
<212> TYPE: DNA
<213> ORGANISM: Artificial Sequence
<220> FEATURE:
<223> OTHER INFORMATION: mab Library

<400> SEQUENCE: 12

```
gatatcgaac tgacccagcc gccgagcgtg agcgtgagcc cgggccagac cgcgagcatt      60
acctgtagcg gcgataaacct gggtgaagaa tacgtttctt ggtaccagca gaaaccgggc    120
```

```
caggcgccgg tgctggtgat ctacgacgac actaaacgtc cgagcggcat cccggaacgt      180
tttagcggat ccaacagcgg caacaccgcg accctgacca ttagcggcac ccaggcggaa      240
gacgaagcgg attattactg cgcttcttgg gacctgtggt ctgttgaagt gtttggcggc      300
ggcacgaagt taaccgttct tggccag                                          327
```

<210> SEQ ID NO 13
<211> LENGTH: 375
<212> TYPE: DNA
<213> ORGANISM: Artificial Sequence
<220> FEATURE:
<223> OTHER INFORMATION: mab Library

<400> SEQUENCE: 13

```
caggtgcaat tggtgcagag cggtgcggaa gtgaaaaaac cgggtgccag cgtgaaagtt      60
agctgcaaag cgtccggata taccttcact tctaacttca tccattgggt gcgccaggcc     120
ccgggccagg gcctcgagtg gatgggctgg atctctccgt acaacggcga cacgaactac     180
gcgcagaaat ttcagggccg ggtgaccatg acccgtgata ccagcattag caccgcgtat     240
atggaactga gccgtctgcg tagcgaagat acggccgtgt attattgcgc gcgtgaatct     300
gtttactacg gttctgacta cggttacaac ggtatggata tctggggcca aggcaccctg     360
gtgactgtta gctca                                                      375
```

<210> SEQ ID NO 14
<211> LENGTH: 9
<212> TYPE: PRT
<213> ORGANISM: Artificial Sequence
<220> FEATURE:
<223> OTHER INFORMATION: mab Library

<400> SEQUENCE: 14

Gly Thr Phe Ser Ser Tyr Ala Ile Ser
1               5

<210> SEQ ID NO 15
<211> LENGTH: 19
<212> TYPE: PRT
<213> ORGANISM: Artificial Sequence
<220> FEATURE:
<223> OTHER INFORMATION: mab Library

<400> SEQUENCE: 15

Met Gly Thr Ile Asp Pro Phe Phe Gly Lys Thr Tyr Tyr Ala Gln Lys
1               5                   10                  15

Phe Gln Gly

<210> SEQ ID NO 16
<211> LENGTH: 19
<212> TYPE: PRT
<213> ORGANISM: Artificial Sequence
<220> FEATURE:
<223> OTHER INFORMATION: mab Library

<400> SEQUENCE: 16

Asp Val Ser Ser Ile Ser Tyr Tyr Phe His Glu Tyr Tyr Ser Asp Arg
1               5                   10                  15

Phe Asp Tyr

<210> SEQ ID NO 17
<211> LENGTH: 14

```
<212> TYPE: PRT
<213> ORGANISM: Artificial Sequence
<220> FEATURE:
<223> OTHER INFORMATION: mab Library

<400> SEQUENCE: 17

Thr Gly Thr Ser Ser Asp Val Gly Gly Tyr Glu Tyr Val Asn
1               5                   10

<210> SEQ ID NO 18
<211> LENGTH: 11
<212> TYPE: PRT
<213> ORGANISM: Artificial Sequence
<220> FEATURE:
<223> OTHER INFORMATION: mab Library

<400> SEQUENCE: 18

Leu Met Ile Tyr Asp Asp Ser Tyr Arg Pro Ser
1               5                   10

<210> SEQ ID NO 19
<211> LENGTH: 9
<212> TYPE: PRT
<213> ORGANISM: Artificial Sequence
<220> FEATURE:
<223> OTHER INFORMATION: mab Library

<400> SEQUENCE: 19

Gln Ser Thr Asp Pro His Ser Thr Val
1               5

<210> SEQ ID NO 20
<211> LENGTH: 112
<212> TYPE: PRT
<213> ORGANISM: Artificial Sequence
<220> FEATURE:
<223> OTHER INFORMATION: mab Library

<400> SEQUENCE: 20

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Glu Tyr Val Asn Trp Tyr Gln Gln His Pro Gly Lys Ala Pro Lys Leu
        35                  40                  45

Met Ile Tyr Asp Asp Ser Tyr Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gln Ser Thr Asp Pro His
                85                  90                  95

Ser Thr Val Val Phe Gly Gly Gly Thr Lys Leu Thr Val Leu Gly Gln
            100                 105                 110

<210> SEQ ID NO 21
<211> LENGTH: 128
<212> TYPE: PRT
<213> ORGANISM: Artificial Sequence
<220> FEATURE:
<223> OTHER INFORMATION: mab Library

<400> SEQUENCE: 21

Gln Val Gln Leu Val Gln Ser Gly Ala Glu Val Lys Lys Pro Gly Ser
1               5                   10                  15
```

-continued

```
Ser Val Lys Val Ser Cys Lys Ala Ser Gly Gly Thr Phe Ser Ser Tyr
        20                  25                  30

Ala Ile Ser Trp Val Arg Gln Ala Pro Gly Gln Gly Leu Glu Trp Met
            35                  40                  45

Gly Thr Ile Asp Pro Phe Phe Gly Lys Thr Tyr Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Val Ser Ser Ile Ser Tyr Tyr Phe His Glu Tyr Tyr Ser
            100                 105                 110

Asp Arg Phe Asp Tyr Trp Gly Gln Gly Thr Leu Val Thr Val Ser Ser
            115                 120                 125
```

<210> SEQ ID NO 22
<211> LENGTH: 336
<212> TYPE: DNA
<213> ORGANISM: Artificial Sequence
<220> FEATURE:
<223> OTHER INFORMATION: mab Library

<400> SEQUENCE: 22

```
gatatcgcgc tgacccagcc ggcgagcgtg agcggtagcc cgggccagag cattaccatt      60
agctgcaccg gcaccagcag cgatgtgggc ggttacgaat acgtgaactg gtaccagcag     120
catccgggca aggcgccgaa actgatgatc tacgacgact cttaccgtcc gagcggcgtg     180
agcaaccgtt ttagcggatc caaaagcggc aacaccgcga gcctgaccat tagcggcctg     240
caagcggaag acgaagcgga ttattactgc cagtctactg acccgcattc tactgttgtg     300
tttggcggcg gcacgaagtt aaccgtccta ggtcag                              336
```

<210> SEQ ID NO 23
<211> LENGTH: 384
<212> TYPE: DNA
<213> ORGANISM: Artificial Sequence
<220> FEATURE:
<223> OTHER INFORMATION: mab Library

<400> SEQUENCE: 23

```
caggtgcaat tggtgcagag cggtgccgaa gtgaaaaaac cgggcagcag cgtgaaagtt      60
agctgcaaag catccggagg gacgtttagc agctatgcga ttagctgggt gcgccaggcc     120
ccgggccagg gcctcgagtg gatgggcact atcgacccgt tcttcggcaa aacttactac     180
gcccagaaat ttcagggccg ggtgaccatt accgccgatg aaagcaccag caccgcctat     240
atggaactga gcagcctgcg cagcgaagat acggccgtgt attattgcgc gcgtgacgtt     300
tcttctatct cttactactt ccatgaatac tactctgacc gtttcgatta ctggggccaa     360
ggcaccctgg tgactgttag ctca                                             384
```

ANTAGONISTS OF IL-17C FOR THE TREATMENT AND/OR PREVENTION OF ATOPIC DERMATITIS

This patent application is the National Stage of International Application No. PCT/EP2016/073776 filed Oct. 5, 2016, which claims the benefit of EP 15188355.0 filed Oct. 5, 2015 each of which is incorporated by reference in its entirety.

FIELD OF THE INVENTION

The present application relates to the treatment and/or prevention of atopic dermatitis and related conditions. More specifically, the invention relates to the administration of antagonists of IL-17C to treat or prevent atopic dermatitis in a patient in need thereof.

BACKGROUND

Atopic dermatitis (AD) is a chronic/relapsing inflammatory skin disease characterized by symptoms including intense pruritus (e.g., severe itch) and by scaly and dry eczematous lesions. Severe disease can be extremely disabling due to major psychological problems, significant sleep loss, and impaired quality of life, leading to high socioeconomic costs. The pathophysiology of AD is influenced by a complex interplay between Immunoglobulin E (IgE)-mediated sensitization, the immune system, and environmental factors. The primary skin defect may be an immunological disturbance that causes IgE-mediated sensitization, with epithelial-barrier dysfunction that is the consequence of both genetic mutations and local inflammation. AD often begins in childhood before age 5 and may persist into adulthood.

Typical treatments for AD include topical lotions and moisturizers, topical corticosteroid ointments, creams or injections. Most treatment options, however, offer only temporary, incomplete, symptom relief. Moreover, many patients with moderate-to-severe AD become resistant to treatment by topical corticosteroids or by calcineurin inhibitors. Thus, a need exists in the art for novel targeted therapies for the treatment and/or prevention of AD.

IL-17C is a secreted homodimer of the IL-17 protein family that was first cloned in 2000 (Li. et al. (2000). Proc. Natl. Acad. Sci. U.S.A. 97, 773-8). It was shown in vitro that IL-17C stimulates the release of TNF-α and IL-1β from the monocytic cell line THP-1 and induces the mRNA expression of inflammatory cytokines such as IL-1β, IL-6 and IL-23 in peritoneal exudate cells (PECs) and the 3T3 cell line (Yamaguchi et al. (2007) J. Immunol 179, 7128-36).

The role of IL-17C as a proinflammatory cytokine relevant for host defense was postulated in several studies (Chang et al. (2011) Immunity 35, 611-621, Song et al. (2011) Nature Immunology 12, 12, Ramirez-Carrozzi et al. (2011) Nature Immunology 12, 12). Also a potential role in the progression of specific tumours and cancerous tissues was recently shown (Song et al. (2014) Immunity 40, 140-152). Only recently, it was demonstrated that the IL-17RE/IL17-RA complex, preferentially expressed in epithelial cells, is the functional receptor for IL-17C and that epithelial cells are the predominant source of IL-17C.

In addition, antibodies that antagonize IL-17C were disclosed (e.g. in WO 1999/060127, WO 2013/057241) and it was demonstrated that antagonists of IL-17C are effective in the treatment of auto-inflammatory disorders, such as rheumatoid arthritis or psoriasis.

SUMMARY OF THE INVENTION

The present invention relates to the surprising findings that an IL-17C antagonist can be used for the treatment and/or prevention of AD and related conditions.

IL-17C was described as a target for treating specific auto-inflammatory disorders. However such disorders, like rheumatoid arthritis or psoriasis are driven by Type 1 (Th1)/Type 17 (Th17) T helper cells.

The present invention identifies Atopic dermatitis (AD) as an indication for an IL-17C antagonist. Recent publication do not suggest nor mention Atopic dermatitis (AD) as a disorder which is potentially treatable by antagonizing IL-17C. In contrast to the Th1 driven disorders, such as rheumatoid arthritis or psoriasis the asymptomatic skin of AD patients is abnormally infiltrated by Th2 cells. Furthermore, Atopic dermatitis (AD) does not respond significantly to anti-Th1 therapies, further suggesting that AD is a "Th2 disease." Therefore an effect of IL-17C antagonists as exemplified in the working examples herein was not expected.

In one aspect, provided herein are antagonists of IL-17C for use in the treatment and/or prevention of AD and related conditions. In one embodiment provided herein are antagonists of IL-17C for use in the treatment and/or prevention of AD. In another embodiment provided herein are antagonists of IL-17C for use in the treatment and/or prevention and/or reduction of the severity of symptoms of atopic dermatitis (AD), including symptoms of moderate-to-severe AD.

In another aspect provided herein are IL-17C antagonists for use in treating or preventing AD, for improving an AD-associated parameter, for decreasing the level of at least one AD-associated biomarker, and/or for treating any of the other indications or conditions disclosed herein, in a subject in need thereof. In one embodiment provided herein are IL-17C antagonists for use in treatment of AD in a subject in need thereof, wherein the treatment results in an improvement in an AD-associated parameter.

In certain embodiments the improvement in the AD-associated parameter is selected from the group consisting of:

(a) a decrease from baseline in Investigator's Global Assessment (IGA) score of at least 40%;
(b) a decrease from baseline in Body Surface Area Involvement of Atopic Dermatitis (BSA) score of at least 40%;
(c) a decrease from baseline in Eczema Area and Severity Index (EASI) score of at least 55%;
(d) a decrease from baseline in SCORAD score of at least 40%;
(e) a decrease from baseline in 5-D Pruritus Scale of at least 25%; and (f) a decrease from baseline in Pruritus Numeric Rating Scale (NRS) score of at least 45%.

In certain embodiments provided herein are antagonists of IL-17C for use in the treatment and/or prevention of AD in a subject in need thereof, comprising administration of a pharmaceutical composition comprising a therapeutically effective amount of an IL-17C antagonist. In certain embodiments, provided herein are antagonists of IL-17C for use in the treatment of moderate-to-severe AD in a subject in need thereof, comprising administering of a pharmaceutical composition comprising a therapeutically effective amount of an antagonists of IL-17C and determining an improvement in an AD-associated parameter. The improvement can be determined or assayed or quantitated by methods well-known in the art. In one embodiment, the subject suffers from moderate-to-severe AD. In some embodiments, the subject suffering from AD is resistant to treatment by either a topical corticosteroid or a calcineurin inhibitor.

In one embodiment, provided herein are antagonists of IL-17C for use in the treatment and/or prevention of AD in a subject in need thereof who is resistant to treatment by a topical corticosteroid or a calcineurin inhibitor. In some embodiments, provided herein are antagonists of IL-17C for use in the treatment and/or prevention of moderate-to-severe AD in a subject in need thereof who is resistant to treatment by a topical corticosteroid or a calcineurin inhibitor. In some embodiments, provided herein are antagonists of IL-17C for use in the treatment of a subject with moderate-to-severe AD that is uncontrolled despite treatment with a topical corticosteroid or a calcineurin inhibitor. The use of the present disclosure comprises administering to a subject in need thereof a pharmaceutical composition comprising a therapeutically effective amount of an IL-17C antagonist.

In certain embodiments, provided herein are IL-17C antagonist as disclosed herein for use in the manufacture of a medicament for the treatment and/or prevention of atopic dermatitis (AD) (e.g., moderate to severe eosinophilic AD, extrinsic AD, intrinsic AD, etc.) or for treating any of the other indications or conditions disclosed herein.

In a certain aspect, provided herein is a composition comprising an IL-17C antagonist capable of antagonizing IL-17C in atopic dermatitis, said composition further comprising one or more pharmaceutically acceptable carriers and/or diluents.

In another aspect, provided herein are antagonists of IL-17C for use in the treatment and/or prevention of AD, wherein said antagonists block the binding of IL-17C to the receptor of IL-17C. In certain aspects, antagonists of IL-17C, such as antibodies specific for IL-17C, may block the binding of IL-17C to IL-17RE. In certain aspects, antagonists of IL-17C, such as antibodies specific for IL-17C blocking the binding of IL-17C to IL-17RE may antagonize any of the roles of IL-17C in atopic dermatitis.

In one aspect the antagonists of IL-17C provided herein may be any antagonist. Preferably, said antagonist is an antibody or antibody fragment, such as a monoclonal antibody. Said antibody may be an antibody or fragment thereof specific for IL-17C or an antibody or fragment thereof specific for the receptor of IL-17C. According to certain embodiments, the IL-17C antagonist is an antibody or antibody fragment that specifically binds IL-17C. Preferably the IL-17C antagonist is an antibody or antibody fragment that specifically binds to human IL-17C. More preferably the IL-17C antagonist is an isolated monoclonal antibody or antibody fragment that specifically binds to human IL-17C. In certain aspects the antagonists of IL-17C provided herein may be an isolated monoclonal antibody or antibody fragment specific for a polypeptide comprising the amino acid sequence of SEQ ID No.: 1. In certain aspects the antagonists of IL-17C provided herein may be an isolated monoclonal antibody or antibody fragment specific for a polypeptide consisting of the amino acid sequence of SEQ ID No.: 1.

In certain aspects, said antibody or antibody fragment specific for IL-17C is a human, humanized or chimeric antibody. In certain aspects, said antibody or antibody fragment specific for IL-17C is a human synthetic antibody. In certain aspects provided herein is an isolated monoclonal antibody or antibody fragment specific for a polypeptide comprising the amino acid sequence of SEQ ID No.: 1 wherein said antibody or antibody fragment is a human, humanized or chimeric antibody. In certain aspects provided herein is an isolated monoclonal antibody or antibody fragment specific for a polypeptide consisting of the amino acid sequence of SEQ ID No.: 1 wherein said antibody or antibody fragment is a human, humanized or chimeric antibody. In certain aspects, said antibody or antibody fragment specific for a polypeptide consisting of the amino acid sequence of SEQ ID No.: 1 is a human synthetic antibody or antibody fragment.

In certain aspects said IL-17C antagonist is an antibody or antibody fragment specific for IL-17C and said antibody or antibody fragment is cross-reactive with IL-17C of another species, such as IL-17C from mouse, rat, rhesus monkey and/or cynomolgus monkey. In certain aspects said IL-17C antibody or antibody fragment is an isolated antibody or antibody fragment specific for IL-17C. In another embodiment said isolated antibody or antibody fragment specific for IL-17C is a monoclonal antibody or antibody fragment. In a further embodiment said isolated monoclonal antibody or antibody fragment is an isolated monoclonal antibody specific for human IL-17C. In a further embodiment said isolated monoclonal antibody or antibody fragment is an isolated monoclonal antibody specific for a polypeptide comprising the amino acid sequence of SEQ ID No.:1. In a further embodiment said isolated monoclonal antibody or antibody fragment is an isolated monoclonal antibody specific for a polypeptide consisting of the amino acid sequence of SEQ ID No.:1. In a further embodiment said isolated monoclonal antibody or antibody fragment is cross-reactive with IL-17C of another species, such as IL-17C from mouse, rat, rhesus monkey and/or cynomolgus monkey.

In another aspect, provided herein are antibodies or antibody fragments specific for IL-17C for use in the treatment and/or prevention of AD, wherein said antibodies or antibody fragments block the binding of IL-17C to a receptor of IL-17C. In certain aspects, said antibodies or antibody fragments specific for IL-17C may block the binding of IL-17C to IL-17RE. In certain aspects, said antibodies or antibody fragments specific for IL-17C, may antagonize any of the roles of IL-17C in atopic dermatitis.

In one embodiment, provided herein are antibodies or antibody fragments specific for IL-17C wherein the antibodies or antibody fragments block the binding of IL-17C to the receptor of IL-17C. In a further embodiment, said antibody or antibody fragment specific for IL-17C blocks the binding of IL-17C to the receptor of IL-17C, wherein said receptor is IL-17RE. In another embodiment the present disclosure refers to an antibody or antibody fragment specific for IL-17C, wherein said antibody or antibody fragment blocks the binding of IL-17C to IL-17RE. In another embodiment said antibody or antibody fragment is an IL-17C antagonist.

In certain embodiments, said antibody or antibody fragment specific for IL-17C blocks the binding of IL-17C to one or more receptors of IL-17C. In alternative embodiments, said antibody or antibody fragment specific for the receptor of IL-17C blocks the binding of IL-17C to receptors of IL-17C, wherein the receptors of IL-17C include IL-17RE and IL-17RA. In alternative embodiments, said antibody or antibody fragment specific for the receptor of IL-17C blocks the binding of IL-17C to IL-17RE and IL-17RA.

In certain embodiments, said antibody or antibody fragment specific for IL-17C blocks the binding of IL-17C to IL-17RE with an $IC_{50}$ concentration of less than 100 nM, 90 nM, 80 nM, 70 nM, 60 nM, 50 nM, 40 nM, 30 nM, 20 nM, 10 nM, 9 nM, 8 nM, 7 nM, 6 nM, 5 nM, 4 nM, 3 nM, 2 nM, 1 nM, 100 pM, 90 pM, 80 pM, 70 pM, 60 pM, 50 pM, 40 pM, 30 pM, 20 pM, 10 pM, 9 pM, 8 pM, 7 pM, 6 pM, 5 pM, 4 pM, 3 pM, 2 pM or 1 pM. In certain aspects the $IC_{50}$ concentration can be determined by ELISA; SET, FACS or MSD (Meso Scale Discovery).

In another aspect, provided herein are antibodies or antibody fragments specific for IL-17C for use in the treatment and/or prevention of AD, wherein said antibodies or antibody fragments block the binding of IL-17C to IL-17RE with an $IC_{50}$ concentration of less than 100 nM, 90 nM, 80 nM, 70 nM, 60 nM, 50 nM, 40 nM, 30 nM, 20 nM, 10 nM, 9 nM, 8 nM, 7 nM, 6 nM, 5 nM, 4 nM, 3 nM, 2 nM, 1 nM, 100 pM, 90 pM, 80 pM, 70 pM, 60 pM, 50 pM, 40 pM, 30 pM, 20 pM, 10 pM, 9 pM, 8 pM, 7 pM, 6 pM, 5 pM, 4 pM, 3 pM, 2 pM or 1 pM. In certain aspects the $IC_{50}$ concentration can be determined by ELISA; SET, FACS or MSD (Meso Scale Discovery).

In one aspect provided herein is a pharmaceutical composition comprising an IL-17C antagonist for use in the treatment and/or prevention of AD and related conditions.

In one aspect provided herein is a pharmaceutical composition comprising an antagonistic antibody or antibody fragment thereof specific for IL-17C for use in the treatment and/or prevention of AD and related conditions.

In a certain embodiment provided herein is a pharmaceutical composition comprising an antagonistic antibody or antibody fragment thereof specific for IL-17C for use in improving one or more AD-associated parameters in a subject in need thereof.

In another embodiment provided herein is a pharmaceutical composition comprising an antagonistic antibody or antibody fragment thereof specific for IL-17C for use in reducing the level of one or more AD-associated biomarkers in a subject in need thereof.

In another embodiment the pharmaceutical composition comprises an antagonistic antibody or antibody fragment thereof specific for IL-17C for use in the treatment of AD in a subject having an elevated level of a biomarker selected from the group consisting of thymus and activation-regulated chemokine (TARC), IgE, eotaxin-3, lactate dehydrogenase (LDH), and periostin.

Other embodiments provided herein will become apparent from a review of the ensuing detailed description.

In certain embodiments, the pharmaceutical composition is administered to the patient before, after or concurrent with a second therapeutic agent. In some embodiments, the second therapeutic agent is a topical corticosteroid (TCS) or a calcineurin inhibitor.

FIGURE LEGENDS

DETAILED DESCRIPTION OF THE INVENTION

Figure 1:
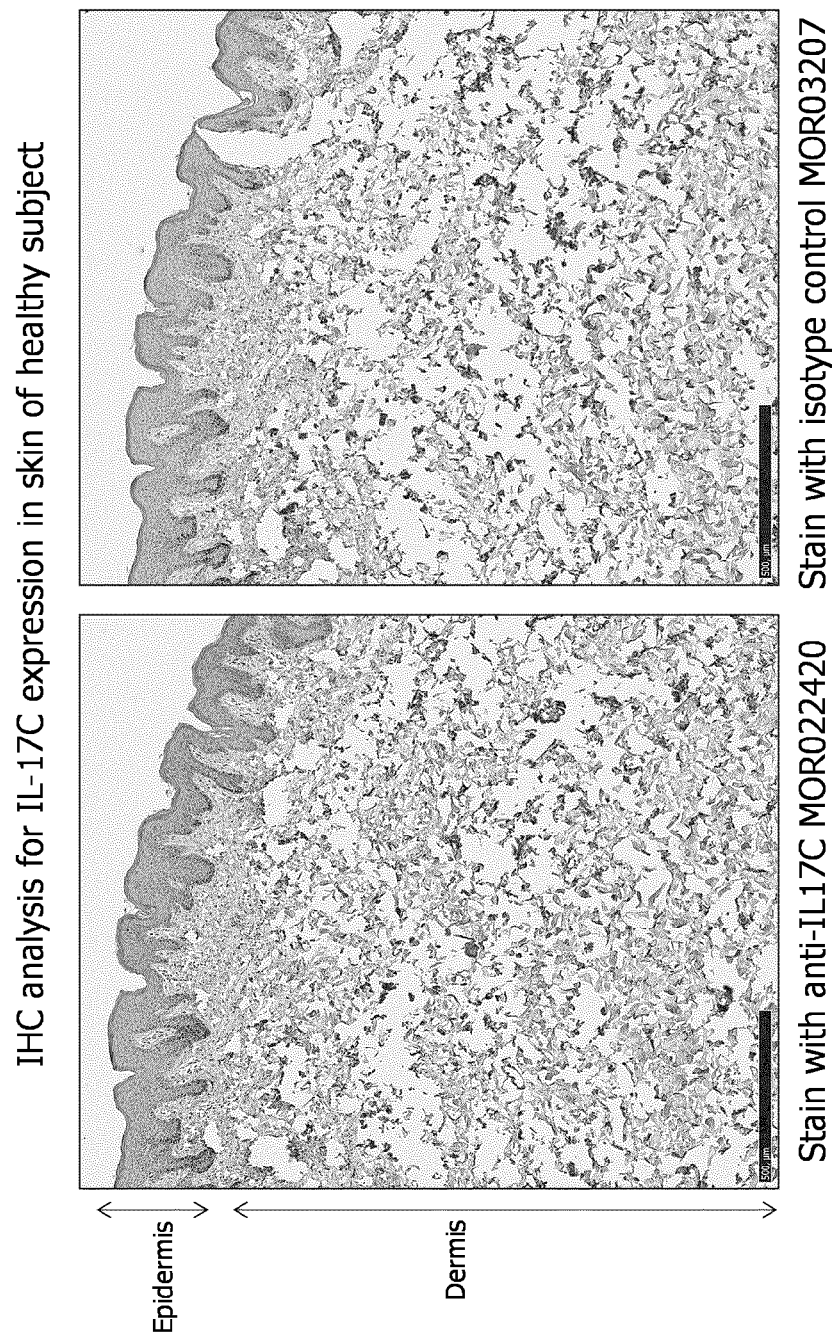
FIG. 1 shows immune-histochemical staining result for IL-17C in the skin of healthy subject.

The present invention demonstrates that IL-17C is a valid target for the treatment and/or prevention of atopic dermatitis. In one aspect provided herein are methods of using an IL-17C antagonist to treat and/or prevent atopic dermatitis and symptoms associated with atopic dermatitis. In another embodiment the therapeutic methods comprise the administration of a therapeutically effective amount of an IL-17C antagonist to a subject in need of such treatment.

A "therapeutically effective amount" or "effective amount", as used herein, refers to the amount of an IL-17C antagonist necessary to elicit the desired biological response. In accordance with the subject disclosure, the therapeutic effective amount is the amount of an IL-17C antagonist necessary to treat and/or prevent atopic dermatitis and symptoms associated with atopic dermatitis.

As used herein, the terms "treat", "treating", or the like, mean to alleviate symptoms, eliminate the causation of symptoms either on a temporary or permanent basis, or to prevent or slow the appearance of symptoms of the named disorder or condition.

As used herein, the terms "subject", "a subject in need thereof" or the like, mean a human or non-human animal that exhibits one or more symptoms or indicia of atopic dermatitis, and/or who has been diagnosed with atopic dermatitis. Preferably the subject is a patient who has been diagnosed with atopic dermatitis. In certain embodiments, the methods may be used to treat patients that show elevated levels of one or more AD-associated biomarkers (described elsewhere herein). For example, the methods provided herein comprise administering an IL-17C antagonist to patients with elevated levels of IgE or TARC or periostin. In some embodiments, the methods herein may be used to treat AD in children who are <1 year old. For example, the present methods may be used to treat infants who are less than 1 month, 1 month, 2 months, 3 months, 4 months, 5 months, 6 months, 7 months, 8 months, 9 months, 10 months, 11 months or less than 12 months old. In other embodiments, the present methods may be used to treat children and/or adolescents who are <18 years old. For example, the present methods may be used to treat children or adolescents less than 17 years, 16 years, 15 years, 14 years, 13 years, 12 years, 11 years, 10 years, 9 years, 8 years, 7 years, 6 years, 5 years, 4 years, 3 years, or less than 2 years old.

The term "Atopic dermatitis" (AD), as used herein, means an inflammatory skin disease characterized by intense pruritus (e.g., severe itch) and by scaly and dry eczematous lesions. The term "Atopic dermatitis" includes, but is not limited to, AD caused by or associated with epidermal barrier dysfunction, allergy (e.g., allergy to certain foods, pollen, mold, dust mite, animals, etc.), radiation exposure, and/or asthma. The present disclosure encompasses methods to treat patients with mild, moderate-to-severe or severe AD. As used herein, "moderate-to-severe AD", is characterized by intensely pruritic, widespread skin lesions that are often complicated by persistent bacterial, viral or fungal infections. Moderate-to-severe AD also includes chronic AD in patients. In many cases, the chronic lesions include thickened plaques of skin, lichenification and fibrous papules. Patients affected by moderate-to-severe AD also, in general, have more than 20% of the body's skin affected, or 10% of skin area in addition to involvement of the eyes, hands and body folds. Moderate-to-severe AD is also considered to be present in patients who require frequent treatment with topical corticosteroids. A patient may also be said to have moderate-to-severe AD when the patient is resistant or refractory to treatment by either a topical corticosteroid or a calcineurin inhibitor or any other commonly used therapeutic agent known in the art.

In certain embodiment provided herein are methods to treat both the extrinsic and the intrinsic forms of AD. The extrinsic form of AD associated with IgE-mediated sensitization and increased levels of Th2 cytokines involves 70% to 80% of patients with AD. The intrinsic form without IgE-mediated sensitization involves 20% to 30% of patients with AD; these patients have lower levels of IL-4 and IL-13 than extrinsic AD.

The term "IL-17C" refers to a protein known as interleukin 17C (identified in HUGO Gene Nomenclature Committee (HGNC) by ID 5983 and in Mouse genome Informatics (MGI) database by ID 2446486). IL-17C is some older publications referred to as CX2 or IL-21, however, it should not be confused with IL-21 cytokine, which is specifically expressed in activated $CD4^+$ T cells, but not most of other tissues (Parrish-Novak et al (2000). Nature 408 (6808): 57-63). Human IL-21 is located on Chromosome 4 and is identified in HGNC database by ID 6005. Human IL-17C is located on Chromosome 16 and has the amino acid sequence of (UniProt Q9P0M4):

(SEQ ID No.: 1)
MTLLPGLLFLTWLHTCLAHHDPSLRGHPHSHGTPHCYSAEELPLGQAPPH

LLARGAKWGQALPVALVSSLEAASHRGRHERPSATTQCPVLRPEEVLEAD

THQRSISPWRYRVDTDEDRYPQKLAFAECLCRGCIDARTGRETAALNSVR

LLQSLLVLRRRPCSRDGSGLPTPGAFAFHTEFIHVPVGCTCVLPRSV

The term "IL-17RA" refers to a protein known as interleukin 17 receptor A. Human IL-17RA has the amino acid sequence of (UniProt Q96F46):

(SEQ ID No.: 2)
MGAARSPPSAVPGPLLGLLLLLLGVLAPGGASLRLLDHRALVCSQPGLNC

TVKNSTCLDDSWIHPRNLTPSSPKDLQIQLHFAHTQQGDLFPVAHIEWTL

QTDASILYLEGAELSVLQLNTNERLCVRFEFLSKLRHHHRRWRFTFSHFV

VDPDQEYEVTVHHLPKPIPDGDPNHQSKNFLVPDCEHARMKVTTPCMSSG

SLWDPNITVETLEAHQLRVSFTLWNESTHYQILLTSFPHMENHSCFEHMH

HIPAPRPEEFHQRSNVTLTLRNLKGCCRHQVQIQPFFSSCLNDCLRHSAT

VSCPEMPDTPEPIPDYMPLWVYWFITGISILLVGSVILLIVCMTWRLAGP

GSEKYSDDTKYTDGLPAADLIPPPLKPRKVWIIYSADHPLYVDVVLKFAQ

FLLTACGTEVALDLLEEQAISEAGVMTWVGRQKQEMVESNSKIIVLCSRG

TRAKWQALLGRGAPVRLRCDHGKPVGDLFTAAMNMILPDFKRPACFGTYV

VCYFSEVSCDGDVPDLFGAAPRYPLMDRFEEVYFRIQDLEMFQPGRMHRV

GELSGDNYLRSPGGRQLRAALDRFRDWQVRCPDWFECENLYSADDQDAPS

LDEEVFEEPLLPPGTGIVKRAPLVREPGSQACLAIDPLVGEEGGAAVAKL

EPHLQPRGQPAPQPLHTLVLAAEEGALVAAVEPGPLADGAAVRLALAGEG

-continued
EACPLLGSPGAGRNSVLFLPVDPEDSPLGSSTPMASPDLLPEDVREHLEG

LMLSLFEQSLSCQAQGGCSRPAMVLTDPHTPYEEEQRQSVQSDQGYISRS

SPQPPEGLTEMEEEEEEQDPGKPALPLSPEDLESLRSLQRQLLFRQLQK

NSGWDTMGSESEGPSA

The term "IL-17RE" refers to a protein known as interleukin 17 receptor E. Human IL-17RE has the amino acid sequence of (UniProt Q8NFR9):

(SEQ ID No.: 3)
MGSSRLAALLLPLLLIVIDLSDSAGIGFRHLPHWNTRCPLASHTDDSFTG

SSAYIPCRTWWALFSTKPWCVRVWHCSRCLCQHLLSGGSGLQRGLFHLLV

QKSKKSSTFKFYRRHKMPAPAQRKLLPRRHLSEKSHHISIPSPDISHKGL

RSKRTQPSDPETWESLPRLDSQRHGGPEFSFDLLPEARAIRVTISSGPEV

SVRLCHQWALECEELSSPYDVQKIVSGGHTVELPYEFLLPCLCIEASYLQ

EDTVRRKKCPFQSWPEAYGSDFWKSVHFTDYSQHTQMVMALTLRCPLKLE

AALCQRHDWHTLCKDLPNATARESDGWYVLEKVDLHPQLCFKFSFGNSSH

VECPHQTGSLTSWNVSMDTQAQQLILHFSSRMHATFSAAWSLPGLGQDTL

VPPVYTVSQARGSSPVSLDLIIPFLRPGCCVLVWRSDVQFAWKHLLCPDV

SYRHLGLLILALLALLTLLGVVLALTCRRPQSGPGPARPVLLLHAADSEA

QRRLVGALAELLRAALGGGRDVIVDLWEGRHVARVGPLPWLWAARTRVAR

EQGTVLLLWSGADLRPVSGPDPRAAPLLALLHAAPRPLLLLAYFSRLCAK

GDIPPPLRALPRYRLLRDLPRLLRALDARPFAEATSWGRLGARQRRQSRL

ELCSRLEREAARLADLG

An "antagonist of IL-17C" and an "IL-17C antagonist", as used herein, refer to IL-17C antagonists in the broadest sense. Any molecule which inhibits the activity or function of IL-17C, or which by any other way exerts an effect on IL-17C is included. The term IL-17C antagonist includes, but is not limited to, antibodies or antibody fragments specifically binding to IL-17C, peptides specific for IL-17C, inhibitory nucleic acids specific for IL-17C or small organic molecules specific for IL-17C. Also within the meaning of the term IL-17C antagonist are antibodies or antibody fragments specifically binding to the receptor of IL-17C, peptides specific for the receptor of IL-17C, inhibitory nucleic acids specific for the receptor of IL-17C or small organic molecules specific for the receptor of IL-17C, wherein the receptors of IL-17C include IL-17RE and/or IL-17RA. The term IL-17C antagonist also refers to non-antibody scaffold molecules, such as fibronectin scaffolds, ankyrins, maxybodies/avimers, protein A-derived molecules, anticalins, affilins, protein epitope mimetics (PEMs) or the like.

Inhibitory nucleic acids include, but are not limited to, antisense DNA, triplex-forming oligonucleotides, external guide sequences, siRNA and microRNA. Useful inhibitory nucleic acids include those that reduce the expression of RNA encoding IL-17C by at least 20, 30, 40, 50, 60, 70, 80, 90 or 95 percent compared to controls. Inhibitory nucleic acids and methods of producing them are well known in the art. siRNA design software is available.

Small organic molecules (SMOLs) specific for IL-17C or the receptor of IL-17C may be identified via natural product screening or screening of chemical libraries. Typically the molecular weight of SMOLs is below 500 Dalton, more typically from 160 to 480 Daltons. Other typical properties of SMOLs are one or more of the following:

The partition coefficient log P is in the range from −0.4 to +5.6

The molar refractivity is from 40 to 130

The number of atoms is from 20 to 70

For reviews see Ghose et al. (1999) J Combin Chem: 1, 55-68 and Lipinski et al (1997) Adv Drug Del Rev: 23, 3-25.

Preferably, an IL-17C antagonist for the use as described herein is an antibody specific for IL-17C or specific for the receptor of IL-17C. More preferably an IL-17C antagonist is an antibody or antibody fragment, such as a monoclonal antibody, specifically binding to IL-17C and blocks the binding of IL-17C to receptors of IL-17C, wherein the receptors of IL-17C include IL-17RE and IL-17RA.

Such an antibody may be of any type, such as a murine, a rat, a chimeric, a humanized or a human antibody. A "human" antibody or functional human antibody fragment is hereby defined as one that is not chimeric (e.g., not "humanized") and not from (either in whole or in part) a non-human species. A human antibody or functional antibody fragment can be derived from a human or can be a synthetic human antibody. A "synthetic human antibody" is defined herein as an antibody having a sequence derived, in whole or in part, in silico from synthetic sequences that are based on the analysis of known human antibody sequences. In silico design of a human antibody sequence or fragment thereof can be achieved, for example, by analyzing a database of human antibody or antibody fragment sequences and devising a polypeptide sequence utilizing the data obtained therefrom. Another example of a human antibody or functional antibody fragment is one that is encoded by a nucleic acid isolated from a library of antibody sequences of human origin (i.e., such library being based on antibodies taken from a human natural source).

A "humanized antibody" or functional humanized antibody fragment is defined herein as one that is (i) derived from a non-human source (e.g., a transgenic mouse which bears a heterologous immune system), which antibody is based on a human germline sequence; or (ii) chimeric, wherein the variable domain is derived from a non-human origin and the constant domain is derived from a human origin or (iii) CDR-grafted, wherein the CDRs of the variable domain are from a non-human origin, while one or more frameworks of the variable domain are of human origin and the constant domain (if any) is of human origin.

The term "chimeric antibody" or functional chimeric antibody fragment is defined herein as an antibody molecule which has constant antibody regions derived from, or corresponding to, sequences found in one species and variable antibody regions derived from another species. Preferably, the constant antibody regions are derived from, or corresponding to, sequences found in humans, e.g. in the human germ line or somatic cells, and the variable antibody regions (e.g. VH, VL, CDR or FR regions) are derived from sequences found in a non-human animal, e.g. a mouse, rat, rabbit or hamster.

In one aspect antigen binding can be performed by "fragments" of an intact antibody. Examples of binding fragments encompassed within the term "antibody fragment" of an antibody include a Fab fragment, a monovalent fragment consisting of the VL, VH, CL and CH1 domains; a F(ab)2 fragment, a bivalent fragment comprising two Fab fragments linked by a disulfide bridge at the hinge region; an Fd fragment consisting of the VH and CH1 domains; an Fv fragment consisting of the VL and VH domains of a single arm of an antibody; a single domain antibody (dAb) fragment (Ward et al., (1989) Nature 341:544-546), which consists of a VH domain; and an isolated complementary determining region (CDR).

A "single chain Fragment (scFv)" is a single protein chain in which the VL and VH regions pair to form monovalent molecules (known as single chain Fv (scFv); see, e.g., Bird et al., (1988) Science 242:423-426; and Huston et al., (1988) Proc. Natl. Acad. Sci. 85:5879-5883). Although the two domains VL and VH are coded for by separate genes, they can be joined, using recombinant methods, by an artificial peptide linker that enables them to be made as a single protein chain. Such single chain antibodies include one or more antigen binding moieties. These antibody fragments are obtained using conventional techniques known to those of skill in the art, and the fragments are screened for utility in the same manner as are intact antibodies.

The term "isolated" refers to a compound which can be e.g. an antibody or antibody fragment that is substantially free of other antibodies or antibody fragments having different antigenic specificities. Moreover, an isolated antibody or antibody fragment may be substantially free of other cellular material and/or chemicals.

The term "monoclonal antibody" as used herein refers to a preparation of antibody molecules of single molecular composition. A monoclonal antibody composition displays a unique binding site having a unique binding specificity and affinity for particular epitopes.

As used herein, an antibody "binds specifically to", "specifically binds to", is "specific to/for" or "specifically recognizes" an antigen (here, IL-17C or, alternatively, the receptor of IL-17C) if such antibody is able to discriminate between such antigen and one or more reference antigen(s), since binding specificity is not an absolute, but a relative property. The reference antigen(s) may be one or more closely related antigen(s), which are used as reference points, e.g. IL17A or IL17B. In its most general form (and when no defined reference is mentioned), "specific binding" is referring to the ability of the antibody to discriminate between the antigen of interest and an unrelated antigen, as determined, for example, in accordance with one of the following methods. Such methods comprise, but are not limited to Western blots, ELISA-, RIA-, ECL-, IRMA-tests and peptide scans. For example, a standard ELISA assay can be carried out. The scoring may be carried out by standard color development (e.g. secondary antibody with horseradish peroxide and tetramethyl benzidine with hydrogen peroxide). The reaction in certain wells is scored by the optical density, for example, at 450 nm. Typical background (=negative reaction) may be 0.1 OD; typical positive reaction may be 1 OD. This means the difference positive/negative can be more than 10-fold. Typically, determination of binding specificity is performed by using not a single reference antigen, but a set of about three to five unrelated antigens, such as milk powder, BSA, transferrin or the like. Additionally, "specific binding" may relate to the ability of an antibody to discriminate between different parts of its target antigen, e.g. different domains or regions of IL-17C or the receptor of IL-17C, or between one or more key amino acid residues or stretches of amino acid residues of IL-17C or the receptor of IL-17C.

"Cross competes" means the ability of an antibody, antibody fragment or other antigen-binding moieties to interfere with the binding of other antibodies, antibody fragments or antigen-binding moieties to a specific antigen in a standard competitive binding assay. The ability or extent to which an antibody, antibody fragment or other antigen-binding moieties is able to interfere with the binding of another antibody, antibody fragment or antigen-binding moieties to a specific antigen, and, therefore whether it can be said to cross-compete according to the present disclosure, can be determined using standard competition binding assays. One suitable assay involves the use of the Biacore technology (e.g. by using the BIAcore 3000 instrument (Biacore, Uppsala, Sweden)), which can measure the extent of interactions using surface plasmon resonance technology. Another assay for measuring cross-competing uses an ELISA-based approach. A high throughput process for "epitope binning" antibodies based upon their cross-competition is described in International Patent Application No. WO 2003/48731. Cross-competition is present if the antibody or antibody fragment under investigation reduces the binding of one of the antibodies described in Table 1 to IL-17C by 60% or more, specifically by 70% or more and more specifically by 80% or more and if one of the antibodies described in Table 1 reduces the binding of said antibody or antibody fragment to IL-17C by 60% or more, specifically by 70% or more and more specifically by 80% or more.

The term "epitope" includes any proteinacious region which is specifically recognized by an immunoglobulin or T-cell receptor or otherwise interacts with a molecule. Generally epitopes are of chemically active surface groupings of molecules such as amino acids or carbohydrate or sugar side chains and generally may have specific three-dimensional structural characteristics, as well as specific charge characteristics. As will be appreciated by one of skill in the art, practically anything to which an antibody can specifically bind could be an epitope. An epitope can comprise those residues to which the antibody binds and may be "linear" or "conformational." The term "linear epitope" refers to an epitope wherein all of the points of interaction between the protein and the interacting molecule (such as an antibody) occur linearly along the primary amino acid sequence of the protein (continuous). The term "conformational epitope" refers to an epitope in which discontinuous amino acids that come together in three dimensional conformations. In a conformational epitope, the points of interaction occur across amino acid residues on the protein that are separated from one another.

Also, as used herein, an "immunoglobulin" (Ig) hereby is defined as a protein belonging to the class IgG, IgM, IgE, IgA, or IgD (or any subclass thereof), and includes all conventionally known antibodies and functional fragments thereof. A "functional fragment" of an antibody/immunoglobulin hereby is defined as a fragment of an antibody/immunoglobulin (e.g., a variable region of an IgG) that retains the antigen-binding region. An "antigen binding region" of an antibody typically is found in one or more hypervariable region(s) of an antibody, i.e., the CDR-1, -2, and/or −3 regions; however, the variable "framework" regions can also play an important role in antigen binding, such as by providing a scaffold for the CDRs. Preferably, the "antigen-binding region" comprises at least amino acid residues 4 to 103 of the variable light (VL) chain and 5 to 109 of the variable heavy (VH) chain, more preferably amino acid residues 3 to 107 of VL and 4 to 111 of VH, and particularly preferred are the complete VL and VH chains (amino acid positions 1 to 109 of VL and 1 to 113 of VH; numbering according to WO 1997/08320). A preferred class of immunoglobulins for use in the present disclosure is IgG. "Functional fragments" include the domain of a F(ab')2 fragment, a Fab fragment, scFv or constructs comprising single immunoglobulin variable domains or single domain antibody polypeptides, e.g. single heavy chain variable domains or single light chain variable domains. The F(ab')2 or Fab may be engineered to minimize or completely remove the intermolecular disulphide interactions that occur between the CH1 and CL domains.

An antibody may be derived from a recombinant antibody library that is based on amino acid sequences that have been designed in silico and encoded by nucleic acids that are synthetically created. In silico design of an antibody sequence is achieved, for example, by analyzing a database of human sequences and devising a polypeptide sequence utilizing the data obtained therefrom. Methods for designing and obtaining in silico-created sequences are described, for example, in Knappik et al., J. Mol. Biol. (2000) 296:57; Krebs et al., J. Immunol. Methods. (2001) 254:67, Rothe et al., J. Mol. Biol. (2008) 376:1182; and U.S. Pat. No. 6,300,064 issued to Knappik et al., which are hereby incorporated by reference in their entirety.

Further Embodiments

In certain aspects, provided herein are methods for the treatment and/or prevention of atopic dermatitis and symptoms associated with atopic dermatitis, said method comprising the step of administering to a subject in need thereof an IL-17C antagonist, wherein said IL-17C antagonist can bind to IL-17C with an affinity of about less than 100 nM, more preferably less than about 60 nM, and still more preferably less than about 30 nM. Further preferred are antibodies or antibody fragments that bind to IL-17C with an affinity of less than about 10 nM, and more preferably less than about 3 nM.

In another aspect, provided herein is a method for the prevention of atopic dermatitis in a subject in need thereof, said method comprising administering an IL-17C antagonist to said subject. "Prevention" as used in this context refers to methods which aim to prevent the onset of a disease or its symptoms or which delay the onset of a disease or its symptoms.

In certain aspects, the present disclosure provides a composition comprising an IL-17C antagonist useful in the treatment of atopic dermatitis, said composition further comprising one or more pharmaceutically acceptable carriers and/or diluents.

In certain aspects, the present disclosure provides IL-17C antagonists for use in the treatment of atopic dermatitis.

In other aspects, the present disclosure provides the use of an IL-17C antagonist in the preparation of a medicament for the treatment of atopic dermatitis.

In other aspects, the present disclosure provides a method for the treatment and/or prevention of atopic dermatitis in a subject, comprising administering to the subject an antagonist of IL-17C.

In particular aspects, the IL-17C antagonists of the present disclosure are administered subcutaneously. In other aspects, the IL-17C antagonists of the present disclosure are administered intra-venously, intra-articularly or intra-spinally.

In one aspect provided herein is a pharmaceutical composition comprising an IL-17C antagonist for use in the treatment and/or prevention of AD and related conditions. In another embodiment provided herein is a pharmaceutical composition comprising an antagonistic IL-17C antibody or antibody fragment for use in the treatment and/or prevention of AD and related conditions. In another aspect, provided herein is a pharmaceutical composition comprising an antagonistic IL-17C antibody or antibody fragment for use in the treatment and/or prevention of AD, wherein said antagonistic antibody or antibody fragment blocks the binding of IL-17C to a receptor of IL-17C. In certain aspects, said antagonistic antibody or antibody fragment specific for IL-17C may block the binding of IL-17C to IL-17RE. In certain aspects, said antagonistic antibody or antibody fragment specific for IL-17C, may antagonize any of the roles of IL-17C in atopic dermatitis.

The compositions provided herein are preferably pharmaceutical compositions comprising an IL-17C antagonist and a pharmaceutically acceptable carrier, diluent or excipient, for the treatment of an inflammatory disorder. Such carriers, diluents and excipients are well known in the art, and the skilled artisan will find a formulation and a route of administration best suited to treat a subject with the IL-17C antagonists of the present disclosure.

In certain aspects, provided herein is a method for the treatment or prophylaxis of an inflammatory disorder in a subject, comprising the step of administering to the subject an effective amount of an antagonist of IL-17C. In certain aspects said subject is a human patient. In alternative aspects said subject is a rodent, such as a rat or a mouse.

In certain aspects, said antagonist of IL-17C is an antibody or antibody fragment specific for IL-17C. In certain aspects said antagonist is an antibody or antibody fragment specific for a polypeptide comprising the amino acid sequence of SEQ ID No.:1. In alternative aspects, said antagonist of IL-17C is an antibody or antibody fragment specific for the receptor of IL-17C.

In certain aspects, said antibody or antibody fragment specific for IL-17C blocks the binding of IL-17C to the receptor of IL-17C. In alternative aspects, said antibody or antibody fragment specific for the receptor of IL-17C blocks the binding of IL-17C to the receptor of IL-17C.

In certain aspects, said antibody or antibody fragment specific for IL-17C blocks the binding of IL-17C to the receptor of IL-17C, wherein said receptor is IL-17RE. In alternative aspects, said antibody or antibody fragment specific for the receptor of IL-17C blocks the binding of IL-17C to IL-17RE.

In certain aspects, said antibody or antibody fragment specific for IL-17C blocks the binding of IL-17C to IL-17RE with an $IC_{50}$ concentration of less than 100 nM, 90 nM, 80 nM, 70 nM, 60 nM, 50 nM, 40 nM, 30 nM, 20 nM, 10 nM, 9 nM, 8 nM, 7 nM, 6 nM, 5 nM, 4 nM, 3 nM, 2 nM, 1 nM, 100 pM, 90 pM, 80 pM, 70 pM, 60 pM, 50 pM, 40 pM, 30 pM, 20 pM, 10 pM, 9 pM, 8 pM, 7 pM, 6 pM, 5 pM, 4 pM, 3 pM, 2 pM or 1 pM. In certain aspects the $IC_{50}$ concentration can be determined by ELISA; SET, FACS or MSD (Meso Scale Discovery).

In certain aspects, said antibody or antibody fragment specific for IL-17C blocks the binding of IL-17C to one or more receptors of IL-17C. In alternative aspects, said antibody or antibody fragment specific for the receptor of IL-17C blocks the binding of IL-17C to receptors of IL-17C, wherein the receptors of IL-17C include IL-17RE and IL-17RA. In alternative aspects, said antibody or antibody fragment specific for the receptor of IL-17C blocks the binding of IL-17C to IL-17RE and IL-17RA.

In another aspect, the disclosure pertains to an isolated monoclonal antibody or fragment thereof that cross-competes with an antibody described in Table 1 for use in the treatment and/or prevention of AD and related conditions. In a certain embodiment, the disclosure pertains to an isolated monoclonal antibody or fragment thereof that cross-competes with an antibody comprising 6 CDRs of one of the antibodies described in Table 1 for use in the treatment and/or prevention of AD and related conditions. In a certain embodiment, the isolated monoclonal antibody or fragment thereof cross-competes with an antibody described in Table 1 and reduces the specific binding of one of the antibodies described in Table 1 by at least 20%, 30%, 40%, 50%, 60%, 70%, 80% or 90% in an ELISA-based cross-competition. In a certain embodiment, the isolated monoclonal antibody or fragment thereof cross-competes with an antibody described in Table 1 and reduces the specific binding of one of the antibodies described in Table 1 to IL-17C by at least 20%, 30%, 40%, 50%, 60%, 70%, 80% or 90% in an ELISA-based cross-competition.

In another embodiment the disclosure pertains to an isolated monoclonal antibody or fragment thereof for use in the treatment and/or prevention of AD and related conditions, wherein said antibody or antibody fragment cross-competes with an antibody or antibody fragment comprising 6 CDRs, wherein the HCDR1 is the amino acid sequence of SEQ ID No.: 4, the HCDR2 is the amino acid sequence of SEQ ID No.: 5, the HCDR3 is the amino acid sequence of SEQ ID No.: 6, the LCDR1 is the amino acid sequence of SEQ ID No.: 7, the LCDR2 is the amino acid sequence of SEQ ID No.: 8 and the LCDR3 is the amino acid sequence of SEQ ID No.: 9. In another embodiment the present disclosure refers to an antibody or antibody fragment, wherein said antibody or antibody fragment cross-competes with an antibody or antibody fragment comprising the VH according to SEQ ID No.: 11 and the VL according to SEQ ID No.: 10.

In another embodiment the disclosure pertains to an isolated monoclonal antibody or fragment thereof for use in the treatment and/or prevention of AD and related conditions, wherein said antibody or antibody fragment cross-competes with an antibody or antibody fragment comprising 6 CDRs, wherein the HCDR1 is the amino acid sequence of SEQ ID No.: 14, the HCDR2 is the amino acid sequence of SEQ ID No.: 15, the HCDR3 is the amino acid sequence of SEQ ID No.: 16, the LCDR1 is the amino acid sequence of SEQ ID No.: 17, the LCDR2 is the amino acid sequence of SEQ ID No.: 18 and the LCDR3 is the amino acid sequence of SEQ ID No.: 19. In another embodiment the present disclosure refers to an antibody or antibody fragment, wherein said antibody or antibody fragment cross-competes with an antibody or antibody fragment comprising the VH according to SEQ ID No.: 21 and the VL according to SEQ ID No.: 20.

In another embodiment the disclosure pertains to an isolated monoclonal antibody or fragment thereof for use in the treatment and/or prevention of AD and related conditions, wherein said antibody or antibody fragment cross-competes with an antibody or antibody fragment comprising a HCDR1 comprising the amino acid sequence of SEQ ID No.: 4, a HCDR2 comprising the amino acid sequence of SEQ ID No.: 5, a HCDR3 comprising the amino acid sequence of SEQ ID No.: 6, a LCDR1 comprising the amino acid sequence of SEQ ID No.: 7, a LCDR2 comprising the amino acid sequence of SEQ ID No.: 8 and a LCDR3 comprising the amino acid sequence of SEQ ID No.: 9. In another embodiment the present disclosure refers to an antibody or antibody fragment, wherein said antibody or antibody fragment cross-competes with an antibody or antibody fragment comprising the VH according to SEQ ID No.: 11 and the VL according to SEQ ID No.: 10.

In another embodiment the disclosure pertains to an isolated monoclonal antibody or fragment thereof for use in the treatment and/or prevention of AD and related conditions, wherein said antibody or antibody fragment cross-competes with an antibody or antibody fragment comprising a HCDR1 comprising the amino acid sequence of SEQ ID No.: 14, a HCDR2 comprising the amino acid sequence of SEQ ID No.: 15, a HCDR3 comprising the amino acid sequence of SEQ ID No.: 16, a LCDR1 comprising the amino acid sequence of SEQ ID No.: 17, a LCDR2 comprising the amino acid sequence of SEQ ID No.: 18 and a LCDR3 comprising the amino acid sequence of SEQ ID No.: 19. In another embodiment the present disclosure refers to an antibody or antibody fragment, wherein said antibody or antibody fragment cross-competes with an antibody or antibody fragment comprising the VH according to SEQ ID No.: 21 and the VL according to SEQ ID No.: 20.

In a further embodiment the present disclosure refers to an isolated monoclonal antibody or fragment thereof for use in the treatment and/or prevention of AD and related conditions, wherein said antibody or antibody fragment cross-competes with an antibody or antibody fragment comprising the VH according to SEQ ID No.: 11 and the VL according to SEQ ID No.: 10 or with an antibody or antibody fragment comprising the VH according to SEQ ID No.: 21 and the VL according to SEQ ID No.: 20.

In another aspect, the disclosure pertains to an isolated monoclonal antibody or fragment thereof that interacts with (e.g., by binding, stabilizing, spatial distribution) the same epitope as an antibody described in Table 1.

Those skilled in the art will appreciate that all subject-matter described herein is susceptible to variations and modifications other than those specifically described which are included herein. The disclosure also includes all of the steps, features, compositions and compounds referred to or indicated in this specification, individually or collectively, and any and all combinations of any two or more of said steps or features.

According to certain exemplary embodiments, the present disclosure provides methods for improving one or more AD-associated parameter(s) in a subject in need thereof. AD-associated parameters and improvements therein are discussed below.

Improvements in AD-associated parameters include, e.g., a decrease in Investigator's Global Assessment (IGA) score; a decrease in Body Surface Area Involvement of Atopic Dermatitis (BSA) score; a decrease in Eczema Area and Severity Index (EASI) score; a decrease in SCORAD score; a decrease in 5-D Pruritus Scale; and/or a decrease in Pruritus Numeric Rating Scale (NRS) score. In exemplary embodiments, the improvement in an AD-associated parameter is selected from the group consisting of: (i) a decrease from baseline in IGA score of at least 25%; (ii) a decrease from baseline in BSA score of at least 35%; (iii) a decrease from baseline in EASI score of at least 45%; (iv) a decrease from baseline in SCORAD score of at least 30%; (v) a decrease from baseline in 5-D Pruritus scale of at least 15%; (vi) a decrease from baseline in Pruritus NRS score of at least 25%; and (vii) percent responders with ≥50% improvement in EASI (EASI50).

According to other exemplary embodiments, the present disclosure provides methods for treating AD in a subject, the methods comprising: (a) selecting a subject who exhibits an elevated level of at least one AD-associated biomarker; and (b) administering to the subject a pharmaceutical composition comprising a therapeutically effective amount of an IL-17C antagonist. In certain embodiments, the IL-17C antagonist is an antibody or antibody fragment thereof that binds IL-17C. Exemplary AD-associated biomarkers that can be evaluated and/or measured in the context of the present disclosure include, but are not limited to, thymus and activation-regulated chemokine (TARC; also known as CCL17), immunoglobulin E (IgE), eotaxin-3, lactate dehydrogenase (LDH), eosinophils, antigen-specific IgE (e.g., Phadiatop™ test), and periostin. In some embodiments, the methods of the present disclosure comprise determining the level of an AD-associated biomarker in a patient in need thereof, selecting a patient with an elevated level of the AD-associated biomarker, and administering a therapeutically effective amount of an antibody or antibody fragment thereof that specifically binds IL-17C. In some embodiments, the patient is selected by acquiring information about the level of an AD-associated biomarker in a patient. In some embodiments, the level of an AD-associated biomarker is determined by an assay or test known in the art or as disclosed elsewhere herein. In one embodiment, the patient is selected on the basis of exhibiting an IgE level greater than about 1500 kU/L prior to or at the time of treatment. In one embodiment, the patient is selected on the basis of exhibiting a TARC level of greater than about 1000 pg/mL prior to or at the time of treatment. According to a related aspect of the present disclosure, methods for treating AD are provided which comprise administering to a subject a pharmaceutical composition comprising a therapeutically effective amount of an IL-17C antagonist, wherein administration of the pharmaceutical composition to the subject results in a decrease in at least one AD-associated biomarker by day 4, 8, 15, 22, 25, 29, 36 or later in the subject following administration. In certain embodiments, the patient exhibits between 5% and 20% decrease in IgE level from the baseline at day 36 or later following administration. In certain embodiments, the patient exhibits between 25% and 70% decrease in TARC level from baseline at day 4 or later following administration.

Also provided herein are methods for decreasing the level of one or more AD-associated biomarker(s) in a subject, or improving one or more AD-associated parameter(s) in a subject, wherein the methods comprise sequentially administering to a subject in need thereof a single initial dose of a pharmaceutical composition comprising an IL-17C antagonist, followed by one or more secondary doses of the pharmaceutical composition comprising the IL-17C antagonist.

In some embodiments, the present disclosure provides methods for treating moderate-to-severe AD comprising concomitant administration of an IL-17C antagonist and a topical corticosteroid (TCS). In some embodiments, the methods further comprise assaying for an improvement in an AD-associated parameter. In certain embodiments, the disclosure provides for methods for improving one or more AD-associated parameters, the methods comprising concomitantly administering an IL-17C antagonist and a TCS, wherein an improvement in an AD-associated parameter is selected from the group consisting of: (i) a decrease from baseline in IGA score of at least 45%; (ii) a decrease from baseline in BSA score of at least 40%; (iii) a decrease from baseline in EASI score of at least 65%; (iv) a decrease from baseline in SCORAD score of at least 50%; (v) a decrease from baseline in 5-D Pruritus scale of at least 25%; and (vi) a decrease from baseline in Pruritus NRS score of at least 60%. In some embodiments, the improvement in an AD-associated parameter is a decrease from baseline in IGA of at least 50% on day 29 after administration of the antibody or antibody fragment thereof that binds IL-17C. In some embodiments, the improvement in an AD-associated parameter is a decrease from baseline in NRS of at least 65% on day 29 after administration. In some embodiments, the improvement in an AD-associated parameter is a decrease from baseline in EASI of at least 70% on day 29 after administration. In some embodiments, the improvement in an AD-associated parameter is a decrease from baseline in SCORAD of at least 60% on day 29 after administration.

In certain embodiments, the topical corticosteroid (TCS) is selected from the group consisting of a group I TCS, a group II TCS and a group III TCS. In some embodiments, the TCS is selected from the group consisting of methylprednisolone aceponate, mometasone furoate, fluticasone propionate, betamethasone valerate and hydrocortisone butyrate.

In related embodiments, provided herein are methods to reduce the dependence on TCS in a patient with moderate-to-severe AD comprising concomitant administration of an IL-17C antagonist and a TCS, wherein the dosage of the TCS is reduced by 50% as compared to subjects without the administration of the IL-17C antagonist. In one embodiment, provided herein are methods to reduce the dosage of a TCS in treatment of moderate-to-severe AD, comprising administration of an IL-17C antagonist concomitantly with a reduced dosage of the TCS. The dosage of the TCS may be reduced by more than, for example, 10%, 20%, 30%, 40%, or 50%. In one embodiment, the dosage of the TCS may be reduced by more than, for example, 10%, 20%, 30%, 40%, or 50% as compared to the dosage used by the subject before treatment with the IL-17C antagonist.

In another aspect, provided herein are methods of monitoring the effectiveness of treatment of moderate-to-severe AD in a subject with an IL-17C antagonist, the method comprising:
(a) determining the expression level of an AD-associated biomarker, such as TARO or serum IgE in a biological sample acquired from the subject before treatment with the IL-17C antagonist;
(b) determining the expression level of one or both of TARO and serum IgE in a biological sample acquired from the subject after treatment with the IL-17C antagonist;
(c) comparing the level determined in step (a) with the level in step (b); and (d) concluding that the treatment is effective when the level determined in step (b) is lower than the level determined in step (a), or concluding that the treatment is not effective when the level determined in step (b) is the same or higher than the level determined in step (a). In one embodiment, the level in step (b) is determined 1 week, 2 weeks, 3 weeks, 4 weeks, or 5 weeks after determining the level in step (a). In one embodiment, the biomarker is TARO, and if TARO levels decrease following administration of the IL-17C antagonist, then treatment with the IL-17C antagonist is determined to be effective.

The expression level of the biomarker can be determined, for example, 1 week, 2 weeks, 3 weeks, 4 weeks, 5 weeks, or longer after administration of the IL-17C antagonist, and compared to the expression level prior to administration of the antagonist. The dose or the dosing regimen of the IL-17C antagonist (e.g., an antibody specific for IL-17C) can be adjusted following the determination. For example, if the expression of the biomarker fails to decrease within 1 week, 2 weeks, 3 weeks, 4 weeks, 5 weeks, or longer following administration of the antagonist, then treatment with the antagonist can be stopped, or the dose of the antagonist can be increased. If expression of the biomarker decreases following administration of the antagonist, the dosage of the antagonist can be maintained or decreased, such as to identify a minimal effective dose. In some embodiments, treatment is maintained at the minimal effective dose.

In another aspect, provided herein are methods for monitoring a subject's response to treatment with an IL-17C antagonist, wherein the subject has moderate-to-severe AD, the method comprising: (a) acquiring information regarding the expression level of one or both of TARC and IgE in a biological sample from the subject following administration of the IL-17C antagonist to the subject; and (b) providing an indication that the treatment should be continued if the expression level of TARC or IgE has decreased as compared to the level before treatment with the IL-17C antagonist. In one embodiment the biomarker is TARC, and if TARC levels are determined to decrease following administration of the antagonist, then an indication is provided to continue treatment with the IL-17C antagonist.

In another aspect, provided herein is a method of treating moderate-to-severe atopic dermatitis (AD) in a patient resistant, non-responsive or inadequately responsive to treatment by either a topical corticosteroid (TCS) or a calcineurin inhibitor, the method comprising administering a pharmaceutical composition comprising a therapeutically effective amount of an IL-17C antagonist to the patient.

In another aspect, provided herein is a method of treating moderate-to-severe atopic dermatitis (AD) in a patient, the method comprising administering a pharmaceutical composition comprising a therapeutically effective amount of an IL-17C antagonist to the patient, wherein the administration of the IL-17C antagonist to the patient results in an improvement in an AD-associated parameter, wherein the improvement in the AD-associated parameter is selected from the group consisting of:
(a) a decrease from baseline in Investigator's Global Assessment (IGA) score of at least 40%;
(b) a decrease from baseline in Body Surface Area Involvement of Atopic Dermatitis (BSA) score of at least 40%;
(c) a decrease from baseline in Eczema Area and Severity Index (EASI) score of at least 55%;
(d) a decrease from baseline in SCORAD score of at least 40%;
(e) a decrease from baseline in 5-D Pruritus Scale of at least 25%; and
(f) a decrease from baseline in Pruritus Numeric Rating Scale (NRS) score of at least 45%.

In another aspect, provided herein is a method of treating moderate-to-severe atopic dermatitis (AD) in a patient resistant, non-responsive or inadequately responsive to treatment by either a topical corticosteroid (TCS) or a calcineurin inhibitor, the method comprising administering a pharmaceutical composition comprising a therapeutically effective amount of an IL-17C antagonist to the patient, wherein the administration of the IL-17C antagonist to the patient results in an improvement in an AD-associated parameter, wherein the improvement in the AD-associated parameter is selected from the group consisting of:
(a) a decrease from baseline in Investigator's Global Assessment (IGA) score of at least 40%;
(b) a decrease from baseline in Body Surface Area Involvement of Atopic Dermatitis (BSA) score of at least 40%;
(c) a decrease from baseline in Eczema Area and Severity Index (EASI) score of at least 55%;
(d) a decrease from baseline in SCORAD score of at least 40%;
(e) a decrease from baseline in 5-D Pruritus Scale of at least 25%; and
(f) a decrease from baseline in Pruritus Numeric Rating Scale (NRS) score of at least 45%.

In certain embodiments the improvement in an AD-associated parameter is a decrease from baseline in IGA of at least 45% on day 85 through at least day 197 after administration of the pharmaceutical composition.

In certain embodiments the improvement in an AD-associated parameter is a decrease from baseline in BSA score of at least 50% on day 85 through at least day 197 after administration of the pharmaceutical composition.

In certain embodiments the improvement in an AD-associated parameter is a decrease from baseline in EASI score of at least 60% on day 85 through at least day 197 after administration of the pharmaceutical composition.

In certain embodiments the improvement in an AD-associated parameter is a decrease from baseline in SCORAD score of at least 45% on day 85 through at least day 197 after administration of the pharmaceutical composition.

In certain embodiments the improvement in an AD-associated parameter is a decrease from baseline in 5-D Pruritus Scale of at least 30% on day 85 through at least day 197 after administration of the pharmaceutical composition.

In certain embodiments the improvement in an AD-associated parameter is a decrease from baseline in NRS score of at least 50% through at least the end of week 16 after administration of the pharmaceutical composition.

In another aspect, provided herein is a method for treating, decreasing, reducing, ameliorating or preventing pruritus in a subject in need thereof, the method comprising administering to the subject in need thereof a pharmaceutical composition comprising a therapeutically effective amount of an IL-17C antagonist. In a certain embodiment subject in need thereof is a patient that has AD. In a further embodiment the patient has moderate-to-severe atopic dermatitis (AD). In one embodiment the patient is resistant, non-responsive or inadequately responsive to treatment by either a topical corticosteroid (TCS) or a calcineurin inhibitor. In another embodiment the administration of the pharmaceutical composition to the patient results in a decrease in pruritus as measured by either a decrease from baseline in 5D Pruritus scale of at least 25% or a decrease from baseline in Pruritus Numeric Rating Scale (NRS) score of at least 45%.

In a further embodiment the administration of the pharmaceutical composition to the patient results in an improvement in an AD-associated parameter selected from the group consisting of:
(a) a decrease from baseline in Investigator's Global Assessment (IGA) score of at least 40%;
(b) a decrease from baseline in Body Surface Area Involvement of Atopic Dermatitis (BSA) score of at least 40%;
(c) a decrease from baseline in Eczema Area and Severity Index (EASI) score of at least 55%; and
(d) a decrease from baseline in SCORAD score of at least 40%.

In another aspect, provided herein is a method for treating or preventing AD in a subject in need thereof, the method comprising: (a) selecting a subject in need thereof who exhibits an elevated level of at least one AD-associated biomarker prior to, or at the time of treatment; and (b) administering to the subject in need thereof a pharmaceutical composition comprising a therapeutically effective amount of an IL-17C antagonist.

In another aspect, provided herein is a method for treating or preventing AD in a subject in need thereof resistant, non-responsive or inadequately responsive to either a TCS or a calcineurin inhibitor, the method comprising: (a) selecting a subject in need thereof who exhibits an elevated level of at least one AD-associated biomarker prior to, or at the time of treatment; and (b) administering to the subject in need thereof a pharmaceutical composition comprising a therapeutically effective amount of an IL-17C antagonist. In one embodiment the AD-associated biomarker is IgE. In another embodiment the AD-associated biomarker is Thymus and Activation Regulated Chemokine (TARC). In a further embodiment the subject in need thereof is selected on the basis of exhibiting an IgE level of greater than 2000 kU/L prior to or at the time of treatment ("baseline"). In another embodiment the subject in need thereof is selected on the basis of exhibiting a TARC level of greater than 1000 pg/mL prior to or at the time of treatment ("baseline"). In another embodiment the subject exhibits at least a 5% decrease in IgE level from baseline at day 50 or later following the administration. In another embodiment the subject exhibits at least a 10% decrease in IgE level from baseline at day 50 or later following the administration. In another embodiment the subject exhibits at least a 25% decrease in TARC level from baseline at day 4 or later following the administration. In another embodiment the subject exhibits at least a 70% decrease in TARC level from baseline at day 29 or later following the administration.

In another aspect, provided herein is a pharmaceutical composition comprising an antibody or antibody fragment thereof specific for IL-17C for use in treatment of AD in a subject having an elevated level of an AD-associated biomarker prior to, or at the time of treatment. In one embodiment the AD-associated biomarker is selected from one or both of TARC or serum IgE.

In another aspect, provided herein is a pharmaceutical composition comprising an antibody or antibody fragment thereof specific for IL-17C for use in treatment of AD in a subject, wherein the treatment results in a decrease in an AD-associated biomarker in the subject by day 4, 8, 15, 22, 25, 29 or 36 following treatment as compared to the level of the biomarker in the subject prior to treatment, wherein the AD-associated biomarker is selected from one or both of TARO or serum IgE.

In another aspect, provided herein is a pharmaceutical composition comprising an antibody or antibody fragment thereof specific for IL-17C for use in improving an AD-associated parameter, or for reducing the level of an AD-associated biomarker in a subject, wherein the pharmaceutical composition is sequentially administered to the subject as a single initial dose followed by one or more secondary doses.

TABLE 1

| Antibody# | | SEQ ID No.: | [aa]/DNA |
|---|---|---|---|
| MOR12743 | HCDR1 | SEQ ID No.: 4 | GYTFTSNFIH |
| | HCDR2 | SEQ ID No.: 5 | WMGWISPYNGDTNYAQKFQG |
| | HCDR3 | SEQ ID No.: 6 | ESVYYGSDYGYNGMDI |
| | LCDR1 | SEQ ID No.: 7 | SGDNLGEEYVS |
| | LCDR2 | SEQ ID No.: 8 | LVIYDDTKRPS |
| | LCDR3 | SEQ ID No.: 9 | ASWDLWSVE |
| | VL | SEQ ID No.: 10 | DIELTQPPSVSVSPGQTASITCSGDNLGEEYVSWYQQ KPGQAPVLVIYDDTKRPSGIPERFSGSNSGNTATLTIS GTQAEDEADYYCASWDLWSVEVFGGGTKLTVLGQ |

TABLE 1-continued

| Antibody# | | SEQ ID No.: | [aa]/DNA |
|---|---|---|---|
| | VH | SEQ ID No.: 11 | QVQLVQSGAEVKKPGASVKVSCKASGYTFTSNFIHW VRQAPGQGLEWMGWISPYNGDTNYAQKFQGRVTMT RDTSISTAYMELSRLRSEDTAVYYCARESVYYGSDYG YNGMDIWGQGTLVTVSS |
| | VL (DNA) | SEQ ID No.: 12 | GATATCGAACTGACCCAGCCGCCGAGCGTGAGCG TGAGCCCGGGCCAGACCGCGAGCATTACCTGTAG CGGCGATAACCTGGGTGAAGAATACGTTTCTTGGT ACCAGCAGAAACCGGGCCAGGCGCCGGTGCTGGT GATCTACGACGACACTAAACGTCCGAGCGGCATCC CGGAACGTTTTAGCGGATCCAACAGCGGCAACACC GCGACCCTGACCATTAGCGGCACCCAGGCGGAAG ACGAAGCGGATTATTACTGCGCTTCTTGGGACCTG TGGTCTGTTGAAGTGTTTGGCGGCGGCACGAAGTT AACCGTTCTTGGCCAG |
| | VH (DNA) | SEQ ID No.: 13 | CAGGTGCAATTGGTGCAGAGCGGTGCGGAAGTGA AAAAACCGGGTGCCAGCGTGAAAGTTAGCTGCAAA GCGTCCGGATATACCTTCACTTCTAACTTCATCCAT TGGGTGCGCCAGGCCCCGGGCCAGGGCCTCGAGT GGATGGGCTGGATCTCTCCGTACAACGGCGACAC GAACTACGCGCAGAAATTTCAGGGCCGGGTGACCA TGACCCGTGATACCAGCATTAGCACCGCGTATATG GAACTGAGCCGTCTGCGTAGCGAAGATACGGCCG TGTATTATTGCGCGCGTGAATCTGTTTACTACGGTT CTGACTACGGTTACAACGGTATGGATATCTGGGGC CAAGGCACCCTGGTGACTGTTAGCTCA |
| MOR22420 | HCDR1 | SEQ ID No.: 14 | GTFSSYAIS |
| | HCDR2 | SEQ ID No.: 15 | MGTIDPFFGKTYYAQKFQG |
| | HCDR3 | SEQ ID No.: 16 | DVSSISYYFHEYYSDRFDY |
| | LCDR1 | SEQ ID No.: 17 | TGTSSDVGGYEYVN |
| | LCDR2 | SEQ ID No.: 18 | LMIYDDSYRPS |
| | LCDR3 | SEQ ID No.: 19 | QSTDPHSTV |
| | VL | SEQ ID No.: 20 | DIALTQPASVSGSPGQSITISCTGTSSDVGGYEYVNW YQQHPGKAPKLMIYDDSYRPSGVSNRFSGSKSGNTA SLTISGLQAEDEADYYCQSTDPHSTVVFGGGTKLTVL GQ |
| | VH | SEQ ID No.: 21 | QVQLVQSGAEVKKPGSSVKVSCKASGGTFSSYAISW VRQAPGQGLEWMGTIDPFFGKTYYAQKFQGRVTITA DESTSTAYMELSSLRSEDTAVYYCARDVSSISYYFHE YYSDRFDYWGQGTLVTVSS |
| | VL (DNA) | SEQ ID No.: 22 | GATATCGCGCTGACCCAGCCGGCGAGCGTGAGCG GTAGCCCGGGCCAGAGCATTACCATTAGCTGCACC GGCACCAGCAGCGATGTGGGCGGTTACGAATACG TGAACTGGTACCAGCAGCATCCGGGCAAGGCGCC GAAACTGATGATCTACGACGACTCTTACCGTCCGA GCGGCGTGAGCAACCGTTTTAGCGGATCCAAAAGC GGCAACACCGCGAGCCTGACCATTAGCGGCCTGC AAGCGGAAGACGAAGCGGATTATTACTGCCAGTCT ACTGACCCGCATTCTACTGTTGTGTTTGGCGGCGG CACGAAGTTAACCGTCCTAGGTCAG |
| | VH (DNA) | SEQ ID No.: 23 | CAGGTGCAATTGGTGCAGAGCGGTGCCGAAGTGA AAAAACCGGGCAGCAGCGTGAAAGTTAGCTGCAAA GCATCCGGAGGGACGTTTAGCAGCTATGCGATTAG CTGGGTGCGCCAGGCCCCGGGCCAGGGCCTCGA GTGGATGGGCACTATCGACCCGTTCTTCGGCAAAA CTTACTACGCCCAGAAATTTCAGGGCCGGGTGACC ATTACCGCCGATGAAAGCACCAGCACCGCCTATAT GGAACTGAGCAGCCTGCGCAGCGAAGATACGGCC GTGTATTATTGCGCGCGTGACGTTTCTTCTATCTCT TACTACTTCCATGAATACTACTCTGACCGTTTCGAT TACTGGGGCCAAGGCACCCTGGTGACTGTTAGCTC A |

WORKING EXAMPLES

The following working examples were performed using the antibodies MOR12743 and MOR22420 (see Table 1). Both antibodies specifically bind to murine or human IL-17C respectively and inhibit binding of IL-17C to its receptor IL-17RE. Therefore both antibodies are antagonists of IL-17C in the sense of the present disclosure. MOR12743 is already disclosed and characterized in WO 2013/057241 (U.S. Ser. No. 14/351,162), which is incorporated by reference in its entirety.

Example 1

Immuno-Histochemical Analysis of IL-17C in Ad Skin

4 μm-thick slices from paraffin-embedded skin biopsies from healthy subjects and subjects with atopic dermatitis were analyzed by IHC. Staining for IL-17C expression was performed with biotinylated MOR22420 (and MOR03207 isotype control antibody). In brief, sections were deparaffinised, rehydrated and unmasked by heat epitope antigen retrieval. Endogenous peroxidase was blocked in BLOX- ALL™ Blocking Solution (Vector Laboratories) and nonspecific binding was blocked with 2.5% Horse Serum Blocking Solution (Vector Laboratories). The primary antibodies were incubated for one hour at room temperature. Binding of MOR22420 biotinylated antibody and MOR03207 biotinylated antibody was detected by incubation with Avidin Biotin Peroxidase Complex (Vector Laboratories). The signal was developed using the peroxidase substrate diaminobenzidine tetrahydrochloride (Sigma). Mayer's hematoxylin (BDH) was used for counterstaining before dehydration and mounting of slides.

Figure 2:
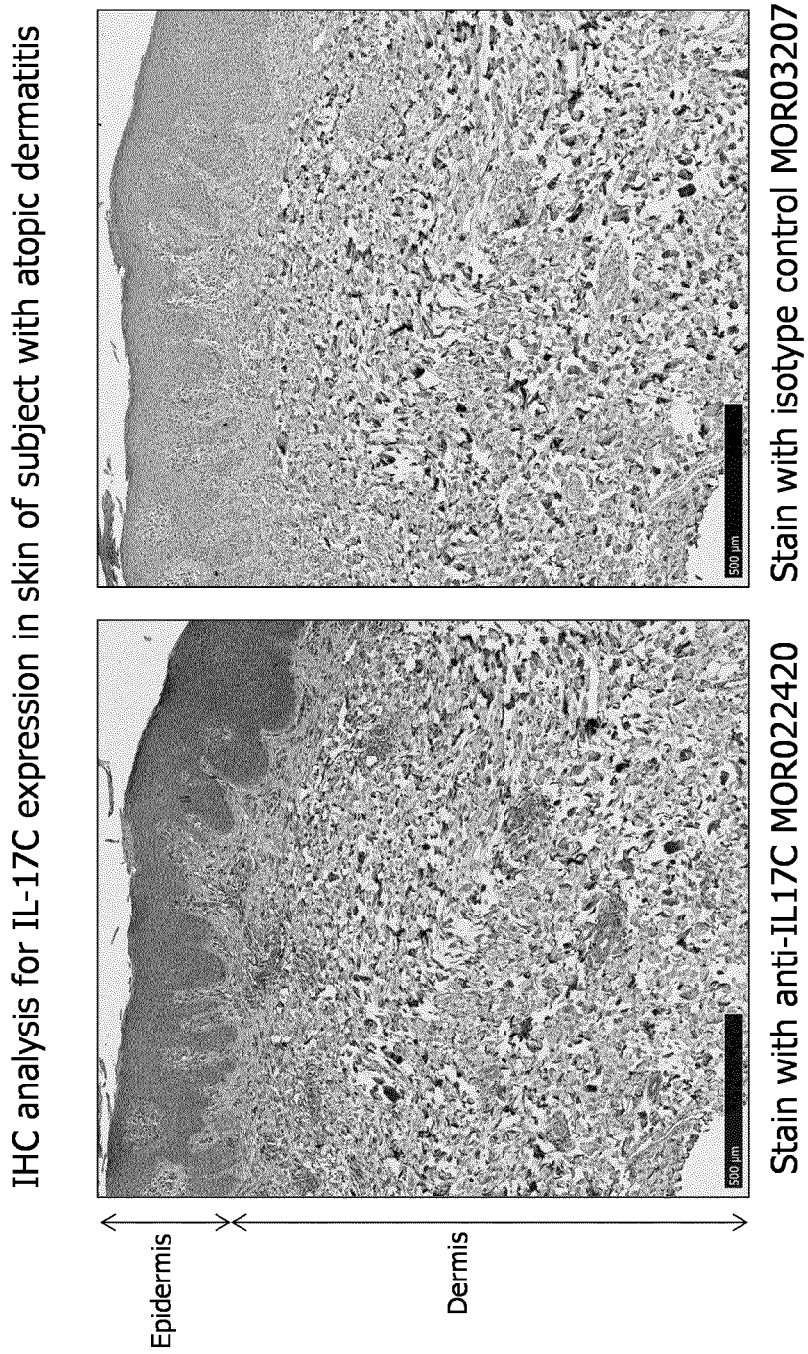
FIG. 2 shows immune-histochemical staining result for IL-17C in the skin of AD patient.

Only a weak staining was detected for IL-17C by immunohistochemistry with the MOR22420 antibody in epidermal keratinocytes of skin of healthy individual (FIG. 1). Expression of IL-17C was highly increased in atopic dermatitis skin (FIG. 2). Expression was increased in keratinocytes, and was detected in vessel endothelial cells and in infiltrated immune cells. Staining was specific and not observed when staining was performed with the MOR03207 negative control antibody.

Example 2

MC903 Mouse Model of Atopic Dermatitis

The pro-inflammatory function of IL-17C in atopic dermatitis was examined in a non-infectious cutaneous inflammation mouse model of atopic dermatitis where topical application of the low-calcemic vitamin D3 analogue MC903 (calcipotriol) induces atopic dermatitis like skin lesion characterized by a red and scaly skin, accompanied by an epidermal hyperplasia and dermal infiltration of various cell types as well as an increase of Th2 cytokine in skin and elevated serum IgE (Li et al., 2006; Li et al, 2009). The MC903 mouse model is a widely accepted and predictable model to mimic the Th2 driven symptoms of atopic dermatitis in vivo.

2.1 Animals

BALB/c mice (female, 8-week old) were obtained from Janvier Labs (France). Mice were kept on a 12 hours light/dark cycle (0700-1900). Temperature was maintained at 22° C., and food and water were provided ad libitum.

2.2. Experimental Procedures

In order to induce an AD-like response, 2 nmol MC903 (Tocris, dissolved in ethanol) was topical applied in a volume of 20 µL on both ears of mice for 5 consecutive days. A non-disease control group received the same quantity of ethanol (EtOH).

The severity of skin inflammation (erythema and thickening) was observed daily. Ear thickness was measured with an electronic caliper (Mitutoyo). Inflammation was further assessed using an in vivo imaging technique. To that end, Prosense 680 probe (1.6 nmol, Perkin Elmer) was administered by intraperitoneal route 24 hours before imaging. Imaging was performed with the Bruker In-vivo Xtreme Imaging System. Images were captured by a deeply cooled 4MP CCD camera (f-stop 1.1, binning 2×2, 5 sec acquisition time, Ex 630 nm, Em 700 nm). For anatomical co-registration, a reflectance image was taken (f-stop 2.8, 0.175 sec acquisition time). All images were taken with a 190×190 field of view and images were analysed using Molecular Imaging Software version 7.1 (Bruker Biospin, Billerica, Mass., USA). For each group, the mean values and standard error of mean (sem) was calculated using for each mouse the mean value of left and right ear.

At sacrifice, samples form ear skin were collected and fixed in 4% formaldehyde before embedding in paraffin. 4 µm-thick slices were stained with hematoxylin and eosin (H&E stain) for histomorphometric evaluation of epidermal thickness by image analysis with Sisn'Com software (France). Five fields per ear (high power field ×20) covering the whole ear from top to bottom were measured, and the 5 values were averaged per ear and per mice (left/right ear). An additional set of tissue slices were prepared for IHC staining of IL-17C using the anti-IL-17C biotinylated MOR12743 antibody (and biotinylated MOR03207 isotype negative control antibody). Processing and staining was essentially done as described above.

Ear skin samples were also taken for analysis of cytokine expression using qPCR or ELISA. Ear tissue pieces for qPCR gene analysis were submerged in RNALater® stabilisation solution (Ambion) and stored at −20° C. Ear skin samples for quantification at protein level were immediately snap frozen in liquid N2 and stored at −80° C. For gene expression analysis, tissue was disrupted and lysed in RNA lysis solution using Precellys homogenisator (microtubes filled with 1.4 mm ceramide beads, 3 times 3 cycles of 15 sec at 6000 rpm). Total RNA was further extracted using NucleoSpin® RNA Kit according to manufactures guidelines (Macherey-Nagel) and 300 ng was reverse-transcribed using Applied Biosystems™ High-Capacity cDNA Reverse Transcription Kit. 5 µL of 10-fold diluted cDNA was used in real-time quantitative PCR reactions using SYBR Green technology with gene-specific primers from Qiagen. qPCR was performed on the ViiA™ 7 Real-Time PCR System (Applied Biosystems). Gene expression was normalized to the expression of 3 different house-keeping genes (cyclophilin, b-actin and GAPDH) and expressed as relative mRNA level of specific gene expression as obtained using the $2^{-\Delta Ct}$ method, with $\Delta Ct = Ct_{gene} - Geomean\ Ct\text{-value}$ (housekeeping genes). For quantification of expression at protein level, tissues were first disrupted and lysed in 250 µL lysis buffer (T-PER™ Tissue Protein Extraction Reagent (Pierce) supplemented with Protease Inhibitor Cocktail (Roche) and Halt™ Phosphatase Inhibitor Cocktail (Pierce)) using Precellys homogenisator (microtubes filled with 2.8 mm metal beads, 10 min 14000 rpm at 4° C.). The amount of TSLP in ears was determined using a TSLP mouse DuoSet ELISA kits from R&D System. The amount was normalized to total protein content in lysate which was determined using Coomassie Protein Assay Reagent (Thermo Fisher) in reference to BSA protein standard. Data were expressed as amount of cytokine in ear which was calculated using the formula: concentration cytokine in sample/concentration of protein in sample×total ear protein content.

The significance of effect of a treatment on each of the readouts was assessed with Prism® Software using one-way ANOVA followed by a Dunnett's multiple comparison post-hoc test versus the MC903+MOR03207 control group with *: $p<0.05$; : $p<0.01$; *: $p<0.001$.

2.3. Study Design

Figure 3:
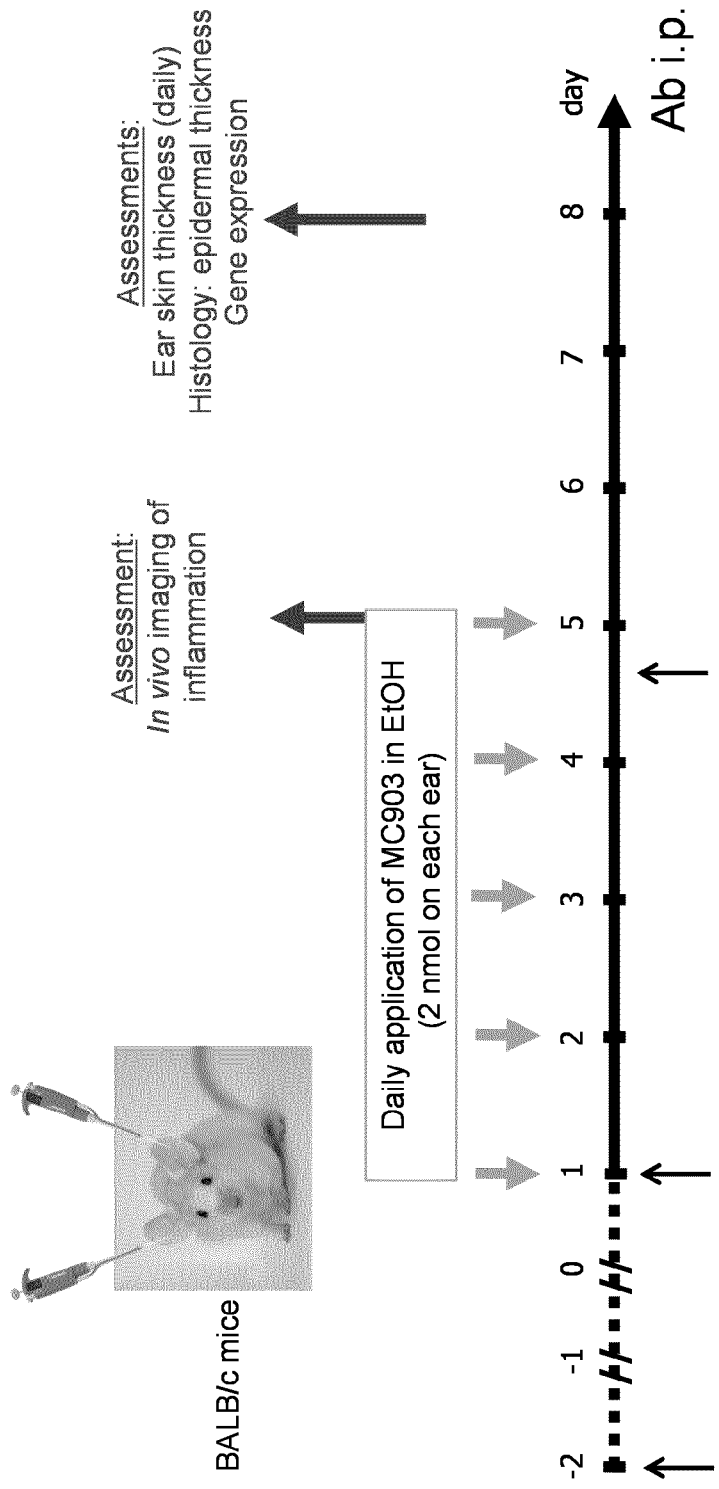
FIG. 3 shows the design of the study for evaluating the efficacy of anti-IL-17C antibody in the MC903 mouse model for AD.

An outline of the study design is given in FIG. 3. Mice were randomly divided into equal groups (n=10). MC903 or EtOH was topical administered on both ears for 5 consecutive days and 3 days later mice were sacrificed. Effect of the anti-IL-17C MOR12743 antibody was compared towards an isotype negative control antibody MOR03207. Both antibodies were formulated in PBS, tested at 10 mg/kg and administered 3 times by intraperitoneal route i.e. 3 days before, at start of and 4 days after the first MC903 application. One group of mice was treated with dexamethasone (DEX) formulated in 0.5% methyl cellulose and administered per os daily from start of MC903 topical application until sacrifice. Therefore, 4 different groups were used:

EtOH+MOR03207 (3×10 mg/kg)
MC903+MOR03207 (3×10 mg/kg)
MC903+MOR12743 (3×10 mg/kg)
MC903+DEX (5 mg/kg p.o. daily)

2.4. Results

Figure 4:
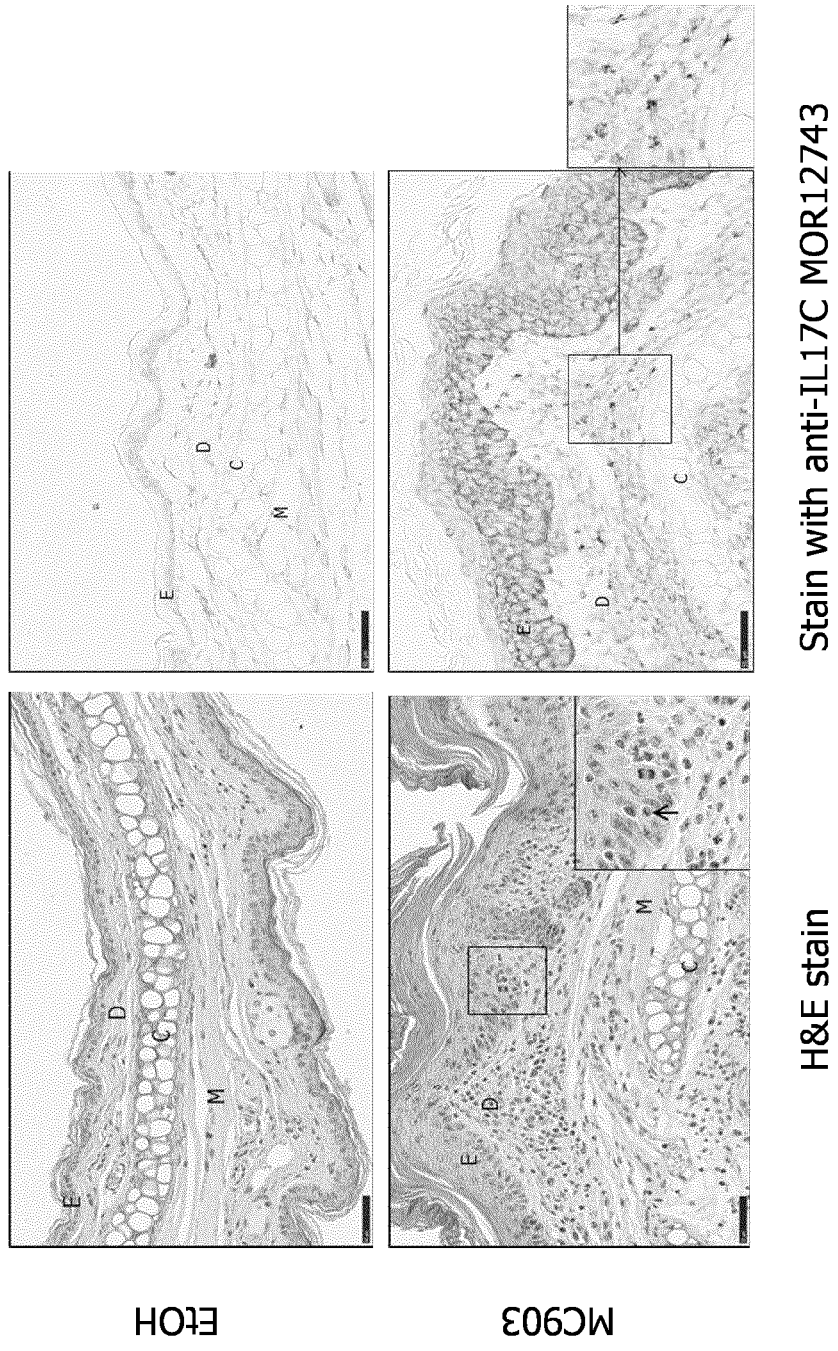
FIG. 4 shows the result for the immune-histochemical staining for IL-17C in skin of MC903 treated mice.

IL-17C was detected by IHC with biotinylated MOR12743 antibody in skin of MC903-treated mice. IL-17C was detected in epidermal keratinocytes and some cells in the dermis (FIG. 4). In contrast, only limited staining was observed in skin of the control group that was treated with EtOH. Staining was specific for IL-17C as no signal was observed with the negative control antibody.

Figure 5:
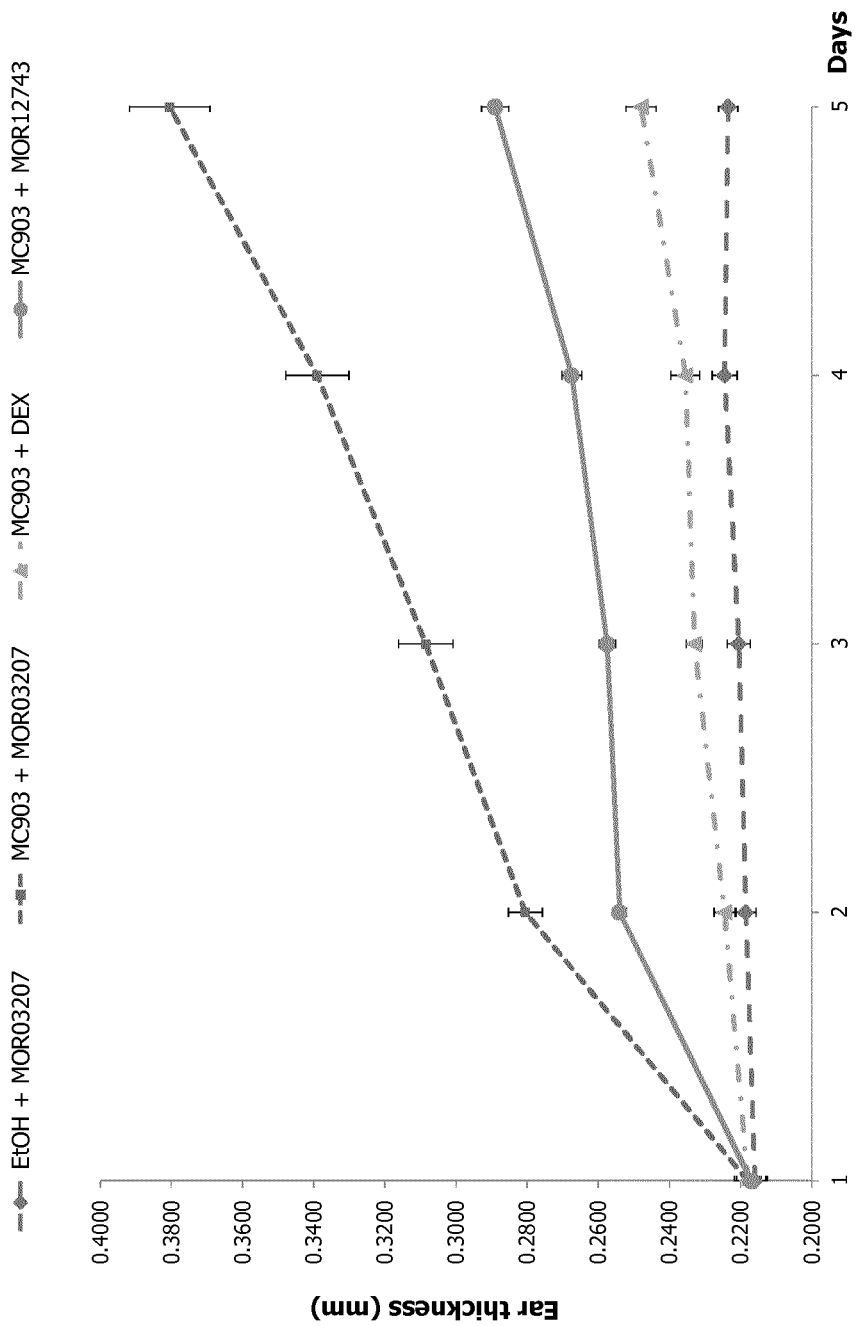
FIG. 5 shows the effect of an antagonistic IL-17C antibody on the development of ear thickness in MC903 induced AD mouse model.
Figure 6:
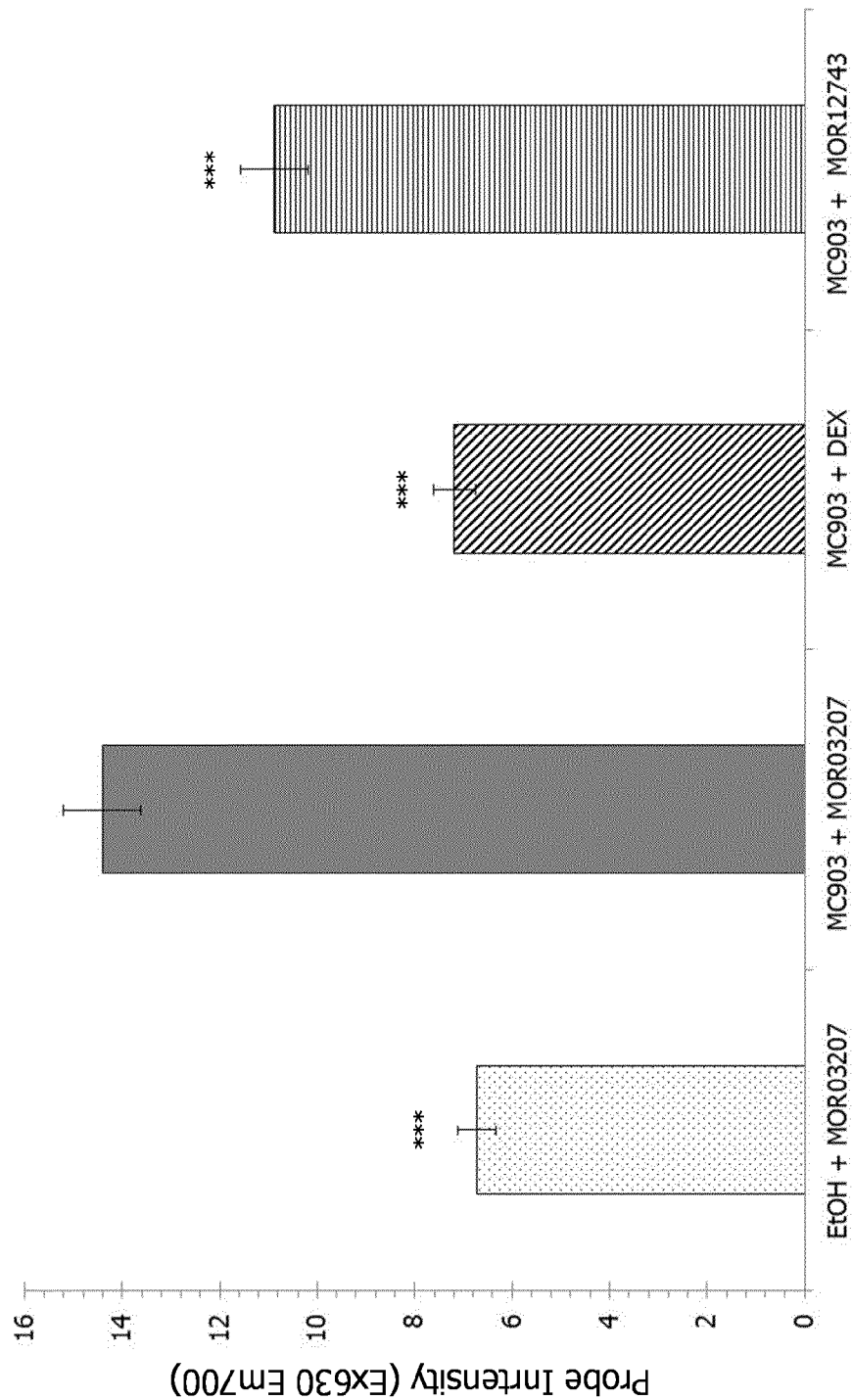
FIG. 6 shows the effect of an antagonistic IL-17C antibody on ear inflammation as assessed by in vivo imaging.
Figure 7:
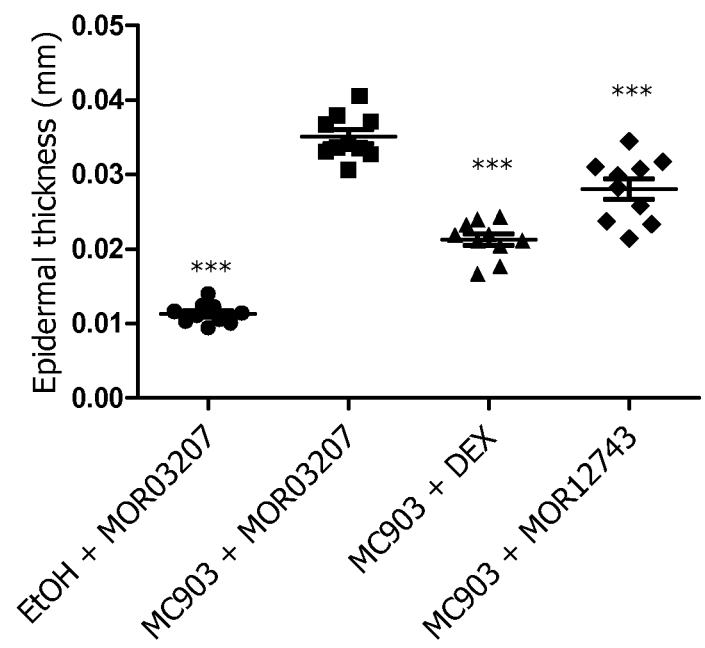
FIG. 7 shows the effect of an antagonistic IL-17C antibody on epidermal thickness in MC903 induced AD mouse model.
Figure 8:
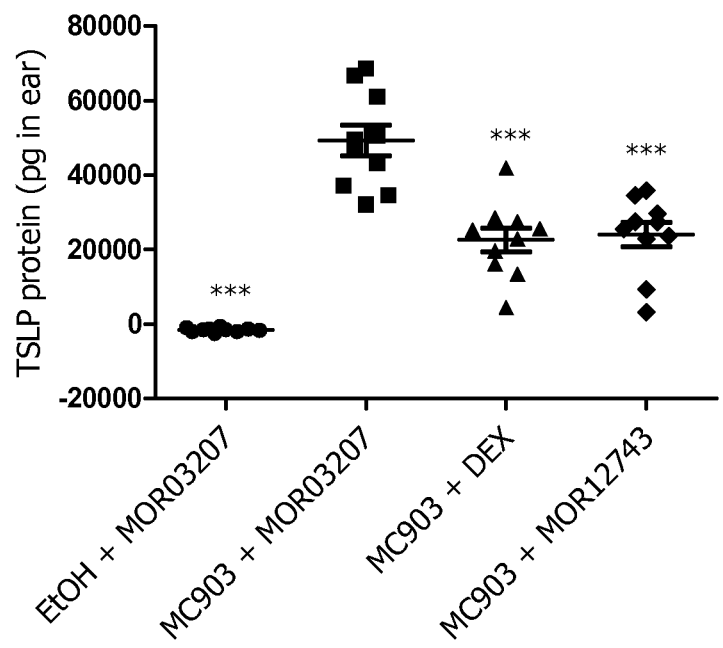
FIG. 8 shows the effect of an antagonistic IL-17C antibody on TSLP protein expression in ears of MC903-treated mice.
Figure 9:
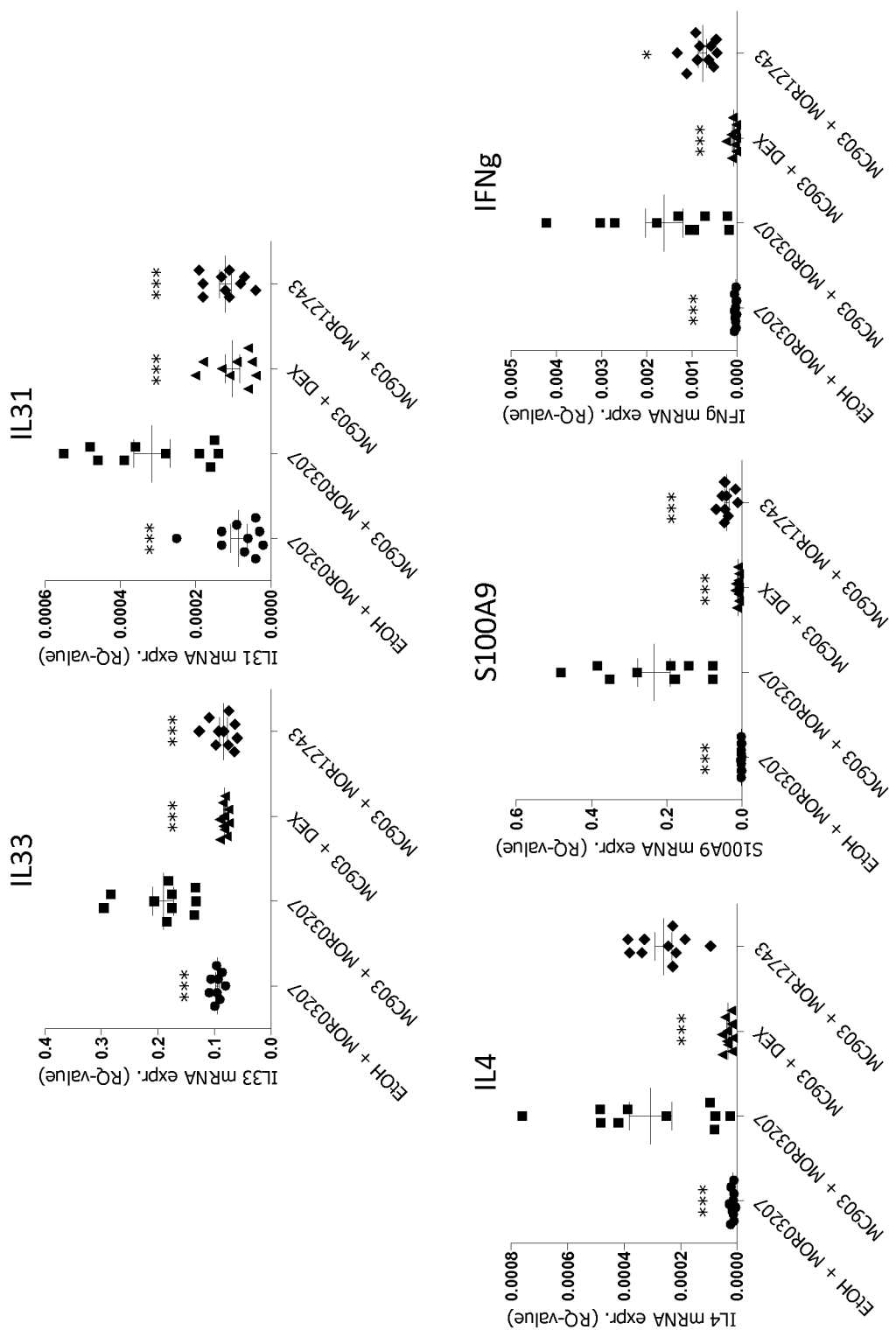
FIG. 9 shows the effect of an antagonistic IL-17C antibody on IL33, IL31, IL4, S100A9 and IFN γ mRNA expression in ears of MC903-treated mice.

After demonstrating that MC903 treatment induced IL-17C expression in mouse ear keratinocytes we evaluated the role of IL-17C in the generation of MC903 induced AD-like skin inflammation by administrating the anti-IL-17C MOR12743 antibody and comparing it towards the effect of an isotype negative control antibody MOR03207. At day 8, ethanol (as vehicle control) had no effect on ears, whereas MC903-treated ears were red (not shown), and swollen. In contrast, MC903-treated ears of MOR12743 treated mice were less red and significantly less swollen (FIG. 5). In line with these observations, ear inflammation as assessed by in vivo imaging at day 5 was increased by MC903-treatment and significantly reduced by MOR12743 treatment (FIG. 6). Histologically, MC903 treated ear skin exhibited a dermal cell infiltrate that included numerous eosinophils and T lymphocytes (not shown) and an epidermal hyperplasia that was partially reduced by MOR12743 treatment (FIG. 7). The involvement of IL-17C in the development of AD skin inflammation was further confirmed by cytokine expression analysis. TSLP expression was highly induced by MC903 treatment and significantly inhibited in MOR12743 treated mice (FIG. 8). A similar effect was also observed on several other AD-relevant genes that were measured and increased by MC903 like IL33, IL31, IL4, S100A9, and IFNg (FIG. 9)

Taken together these data indicate that neutralisation of IL-17C activity precludes the generation of an AD-like skin inflammation upon MC903 topical application and suggest a role for IL-17C in atopic dermatitis. Therefore it is demonstrated for the first time that antibodies specific for IL-17C are effective in the treatment of atopic dermatitis.

REFERENCES

Li M, Hener P., Zhang Z., Kato S., Metzger D and Chambon P. Topical vitamin D3 and low-calcemic analogs induce thymic stromal lymphopoeitin in mouse keratinocytes and trigger an atopic dermatitis. PNAS (2006). 103, 11736-11741

Li M., Hener P., Zhang Z., Ganti K. P., Metzger D and Chambon P. Induction of thymic stromal lymphopoeitin expression in keratinocytes is necessary for generating an atopic dermatitis upon application of the active vitamin D3 analogue MC903 on mouse skin. J. Invest. Dermatol. (2009), 129, 498-502

The invention claimed is:

1. A method for treating atopic dermatitis in a subject in need thereof, said method comprising administering to the subject a pharmaceutical composition comprising a therapeutically effective amount of an IL-17C antibody or antibody fragment comprising a heavy chain complementarity determining region (HCDR) 1 comprising the amino acid sequence of SEQ ID NO:14, a HCDR2 comprising the amino acid sequence of SEQ ID NO:15, a HCDR3 comprising the amino acid sequence of SEQ ID NO:16, a light chain complementarity determining region (LCDR) 1 comprising the amino acid sequence of ID NO:17, a LCDR2 comprising the amino acid sequence of SEQ ID NO:18 and a LCDR3 comprising the amino acid sequence of SEQ ID NO:19.

2. The method of claim 1, wherein the antibody or antibody fragment comprises a variable light ($V_L$) chain as set forth in SEQ ID NO:20 and a variable heavy ($V_H$) chain as set forth in SEQ ID NO:21.

3. The method of claim 2, wherein said pharmaceutical composition is administered subcutaneously or intravenously to the subject in need thereof.

4. The method of claim 2, further comprising administering a second therapeutic agent to the subject before, after, or concurrent with the pharmaceutical composition.

5. The method of claim 4, wherein the second therapeutic agent is selected from the group consisting of a group I topical corticosteroid (TCS), a group II TCS, and a group III TCS.

6. The method of claim 1, wherein the subject is resistant, non-responsive or inadequately responsive to treatment of atopic dermatitis with a TCS or a calcineurin inhibitor.

* * * * *